United States Patent
Locascio et al.

(10) Patent No.: US 8,216,526 B2
(45) Date of Patent: Jul. 10, 2012

(54) METHOD AND DEVICE FOR GENERATING DIFFUSIVE GRADIENTS IN A MICROFLUIDIC CHAMBER

(75) Inventors: Laurie E. Locascio, North Potomac, MD (US); Francisco Javier Atencia-Fernandez, Bethesda, MD (US)

(73) Assignee: The United States of America, as represented by the Secretary of Commerce, The National Institute of Standards and Technology, Washington, DC (US)

( * ) Notice: Subject to any disclaimer, the term of this patent is extended or adjusted under 35 U.S.C. 154(b) by 523 days.

(21) Appl. No.: 12/401,900

(22) Filed: Mar. 11, 2009

(65) Prior Publication Data
US 2009/0311737 A1    Dec. 17, 2009

Related U.S. Application Data

(60) Provisional application No. 61/073,260, filed on Jun. 17, 2008.

(51) Int. Cl.
*G01N 15/06* (2006.01)
*G01N 33/00* (2006.01)
*G01N 33/48* (2006.01)

(52) U.S. Cl. ......... 422/503; 422/50; 422/68.1; 422/502; 422/504; 422/505; 422/509; 422/554; 436/43; 436/63; 436/174

(58) Field of Classification Search ............ 422/50, 422/68.1, 502, 503, 504, 505, 509, 554; 436/43, 436/63, 174
See application file for complete search history.

(56) References Cited

U.S. PATENT DOCUMENTS

| | | | |
|---|---|---|---|
| 5,589,352 A | | 12/1996 | Breznak et al. |
| 5,716,852 A | * | 2/1998 | Yager et al. .................... 436/172 |
| 6,830,936 B2 | * | 12/2004 | Anderson et al. ............. 436/180 |
| 7,306,672 B2 | | 12/2007 | Hansen et al. |
| 2006/0002804 A1 | | 1/2006 | Jiang et al. |
| 2007/0015137 A1 | * | 1/2007 | Zantl ................................. 435/4 |
| 2007/0178582 A1 | * | 8/2007 | Koser .......................... 435/288.5 |
| 2007/0253868 A1 | | 11/2007 | Beebe et al. |
| 2007/0275455 A1 | * | 11/2007 | Hung et al. ................. 435/287.1 |
| 2008/0085219 A1 | | 4/2008 | Beebe et al. |

(Continued)

OTHER PUBLICATIONS

Javier Atencia, Jayne Morrow and Laurie E. Locascio, "The 'Microfluidic Palette': Generation of Stable and Purely Diffusive Chemical Gradients Inside a Microfluidic Chamber." Tweltfh International Conference on Miniaturized Systems for Chemistry and Life Sciences, Oct. 12-16, 2008, San Diego, CA, USA.*

(Continued)

*Primary Examiner* — Brian J Sines
(74) *Attorney, Agent, or Firm* — Rankin, Hill & Clark LLP

(57) ABSTRACT

A microfluidic device is described, capable of generating multiple spatial chemical gradients simultaneously inside a microfluidic chamber. The chemical gradients are generated by diffusion, without convection, and can either be maintained constant over long time periods, or modified dynamically. A representative device is described with a circular chamber in which diffusion occurs, with three access ports for the delivery and removal of solutes. A gradient typically forms in minutes, and can be maintained constant indefinitely. Gradients overlapping with different spatial location, and a controlled rotation of a gradient formed by diffusion are demonstrated. The device can also be used to evaluate chemotactic responses of bacteria or other microorganisms in the absence of convective flow.

19 Claims, 12 Drawing Sheets

U.S. PATENT DOCUMENTS

2008/0190220 A1* 8/2008 Backes et al. ............ 73/864.81

OTHER PUBLICATIONS

Abhyankar V., Lokuta M., Huttenlocher A., Beebe D., "Characterization of a membrane-based gradient generator for use in cell-signaling studies," The Royal Society of Chemistry 2006, pp. 389-393, vol. 6.

Chung B., Flanagan L., Rhee S., Schwartz P., Lee A., Monuki E., Jeon N., "Human neural stem cell growth and differentiation in a gradient-generating microfluidic device," The Royal Society of Chemistry 2005, pp. 401-406, vol. 5.

Diao J., Young L., Kim S., Fogarty E., Heilman S., Zhou P., Shuler M., Wu M., DeLISA M., "A three-channel microfluidic device for generating static linear gradients and its application to the quantitative analysis of bacterial chemotaxis," The Royal Society of Chemistry, pp. 381-388, vol. 6.

Jeon N., Baskaran H., Dertinger S., Whitesides G., Van De Water L., Toner M., "Neutrophil chemotaxis in linear and complex gradients of interleukin-8 formed in a microfabricated device," Nature Biotechnology, Jul. 2002, pp. 826-830, vol. 20.

Keenan T., Folch A., "Biomolecular gradients in cell culture systems," The Royal Society of Chemistry 2008, pp. 34-57, vol. 8.

Keenan T., Hsu C., Folch A., "Microfluidic 'jets' for generating steady-state gradients of soluble molecules on open surfaces," Applied Physics Letters, 2006, pp. 114103-1-114103-3, vol. 89.

Mosadegh B., Huang C., Park, J., Shin H., Chung B., Hwang S., Lee K., Kim H., Brody J., Jeon N., "Generation of Stable Complex Gradients Across Two-Dimensional Surfaces and Three-Dimensional Gels," Langmuir 2007, pp. 10910-10912, vol. 23, American Chemical Society, Washington, D.C.

Paliwal S., Iglesias P., Campbell K., Hilioti Z., Groisman A., Levchenko A., "MAPK-mediated bimodal gene expression and adaptive gradient sensing in yeast," nature, Mar. 2007, pp. 46-51, vol. 446.

Saadi W., Rhee S., Lin F., Vahidi B., Chung B., Jeon N., "Generation of stable concentration gradients in 2D and 3D environments using a microfluidic ladder chamber," Biomed Microdevices 2007, pp. 627-635, vol. 9.

Dertinger S., Chiu D., Jeon N., Whitesides G., "Generation of Gradients Having Complex Shapes Using Microfluidic Networks," Analytical Chemistry, Mar. 15, 2001, pp. 1240-1246, vol. 73, No. 6.

Hansen C., Quake S., "Microfluidics in structural biology: smaller, faster . . . better," Current Opinion in Structural Biology 2003, 538-544, vol. 13.

Hung P., Lee P., Sabounchi P., Aghdam N., Lin R., Lee L., "A novel high aspect ratio microfluidic design to provide a stable and uniform microenvironment for cell growth in a high throughput mammalian cell culture array," The Royal Society of Chemistry 2005, pp. 44-48, vol. 5.

Jeon N., Dertinger S., Chiu D., Choi I., Stroock A., Whitesides G., "Generation of Solution and Surface Gradients Using Microfluidic Systems," Langmuir 2000, pp. 8311-8316, vol. 16.

Lin F., Saadi W., Rhee S., Wang S., Mittal S., Jeon N., "Generation of dynamic temporal and spatial concentration gradients using microfluidic devices," The Royal Society of Chemistry 2004, pp. 164-167, vol. 4.

Walker G., Sai J., Richmond A., Stremler M., Chung C., Wikswo J., "Effects of flow and diffusion on chemotaxis studies in a microfabricated gradient generator," The Royal Society of Chemistry 2005, pp. 611-618, vol. 5.

Javier Atencia, Jayne Morrow and Laurie E. Locasio, "The microfluidic palette: A diffusive gradient generator with spatio-temporal control," The Royal Society of Chemistry, Lab on a Chip, 2009, pp. 2707-2714, vol. 9.

* cited by examiner

NON MOTILE BACTERIA

MOTILE BACTERIA

METHOD AND DEVICE FOR GENERATING DIFFUSIVE GRADIENTS IN A MICROFLUIDIC CHAMBER

CROSS REFERENCES TO RELATED APPLICATIONS

The present application claims priority upon U.S. provisional application Ser. No. 61/073,260 filed on Jun. 17, 2008.

STATEMENT AS TO RIGHTS TO INVENTION(S) MADE UNDER FEDERALLY-SPONSORED RESEARCH AND DEVELOPMENT

The US Government, through the National Institute of Standards and Testing, is the owner of this invention.

FIELD OF INVENTION

The presently disclosed embodiments are directed to the field of microfluidics, methods and applications involving such, and related devices.

BACKGROUND OF THE INVENTION

Chemical gradients generated by the release and diffusion of soluble factors mediate many complex processes in biology. A chemical gradient provides not only information about the existence of a particular signal, but also provides spatial information. For example, a motile cell moving through a gradient in a direction of increasing concentration will eventually find the source of the chemical signal. This process, i.e., the migration of cells towards or away from a source of a chemical signal (chemotaxis), plays a key role in cancer spreading, wound healing, and morphogenesis in the case of eukaryotic cells; and animal infection, plant infection, and carbon cycling in the ocean in the case of prokaryotic cells.

In-vitro models of biochemical gradients have been used to validate cellular models by assessing cellular response to specific soluble signals. Early approaches to study chemotaxis provided a wealth of useful information despite the limitations of having to deal with microscale phenomena using macroscale tools. Microfabrication techniques provide tools that allow for exquisite control over microscale liquid interfaces and in particular, control of chemical gradients. For example, Jeong et al. showed that in a microchannel, under laminar flow and high Peclect number (ratio of convection to diffusion), a cross-sectional concentration profile generated upstream is preserved downstream as it flows over a cell population under study, see N. L. Jeon, H. Baskaran, S. K. W. Dertinger, G. M. Whitesides, L. Van de Water and M. Toner, "Neutrophil Chemotaxis in Linear and Complex Gradients of Interleukin-8 Formed in a Microfabricated Device," *Nat Biotechnol*, Vol. 20, pp. 826-830 (August 2002). Subsequent monitoring of cell motility was correlated with the gradient profile to infer chemotactic behavior.

Due to the relative simplicity of this approach, gradients generated using laminar flow have been used extensively to study chemotaxis of adherent cells. However, a disadvantage of this practice is that cells may be exposed to convective flows which cells may not experience in-vivo. The side effects of such convective flows may include for example, shear stress, the removal of autocrine and paracrine signals secreted by cells, bias on the direction of cellular migration and asymmetrical mass transport, all of which may alter cellular response. In some cases, research has been devoted, if not to eliminate these adverse effects, at least to minimize them. In general, fluid flow is not well suited to analyze chemotaxis of non-adherent cells because instead of flushing soluble signals over the cells, it may flush both signals and cells. An exception is when the object of study is the competition between bacterial migration towards nutrients, against external adverse convection of turbulences.

Recent attempts to generate diffusive gradients in the absence of convective flows have yielded important but partial progress. These approaches include (i) using membranes to restrict flow while allowing diffusion of soluble species, (ii) using valves to bring liquid plugs in contact allowing free diffusion between them; and (iii) different configurations for balancing pressures on both sides of a microchannel. Although each of these elegant approaches has provided valuable insight into chemotaxis, all of them have limitations. Typically they (i) allow only for the diffusion between two solutions (one dimensional); (ii) are static; i.e., once the diffusive interface is established, it can only be modified using convective flows that inevitably disrupt the diffusion profiles; (iii) can operate only for short periods of time; or (iv) have difficult accessibility, in that cells need to be introduced in the chambers before the gradients are generated. The transient development of a gradient can be long and influence cellular response in ways that may not be easily deconvolved.

Prior artisans have devices and strategies for forming gradients. However, these previous efforts have suffered from one or more of the previously noted disadvantages. For example, US Patent Publication 2007/0253868 to Beebe et al. is directed to a microfluidic platform and method for generating a gradient. However, those various devices all utilize one or more membranes to prevent convective flow into a chamber region. As noted, such membranes interfere with extent and rate of diffusion of agents into the chamber. U.S. Pat. No. 7,306,672 to Hansen et al. provides a detailed description of microfluidic devices that provide for diffusion into a chamber or region of interest. However, the devices and systems described by Hansen et al. utilize flow-blocking valves in one or more microfluidic chambers. Upon establishment of static liquids on both sides of a valve, the valve is then opened whereby diffusion can then occur across the resulting liquid interface. Although satisfactory in certain respects, using one or more valves to selectively create such a liquid interface introduces additional variables which may deleteriously affect gradient development and maintenance. Furthermore, requiring the use of moving components in a microfluidic system increases complexity and cost of the system. Additionally, using flow-blocking valves precludes administration of one or more agents from a source into a chamber or other region of interest, while the valve(s) are closed. Moreover, pressure differences between liquids on opposite sides of the valve and opening or closing operations of the valve itself can introduce or generate undesirable convective flows.

Additionally, gels have also been used to prevent convective flows and simultaneously to grow cells in three dimensional scaffolds and other microfluidic devices. However, gels as a result of their high viscosity, are often not appropriate for many investigations.

In view of these various efforts and their limitations, a need exists for a strategy by which gradients may be readily formed and maintained without the previously noted deleterious consequences associated with currently known microfluidic devices and the convective flows that inevitably result therein. Specifically, it would be desirable to provide a process and device for establishing and maintaining one or more gradients exclusively by diffusion and without the use of membranes, flow-blocking valves, or gels.

SUMMARY OF THE INVENTION

The difficulties and drawbacks associated with previous-type systems are overcome in the present methods and devices.

In a first aspect, the present invention provides a microfluidic system comprising a chamber defining an interior region adapted for retaining a liquid. The system also comprises at least three channels adapted to contain and direct liquid when flowing therethrough. Each channel defines an inlet and an outlet. Each of the channels is in fluid communication with the chamber via a respective access port located between the inlet and outlet of the respective channel. The system further comprises at least one flow controller for matching flow rates of liquid flowing in the channels. The system is free from membranes disposed at or proximate the access ports that would otherwise affect fluid communication between a respective channel and the chamber.

In another aspect, the present invention provides a microfluidic system comprising a chamber defining an interior region adapted for retaining a liquid. The system also comprises at least three channels adapted to contain and direct liquid when flowing therethrough. Each of the channels is in fluid communication with the chamber via a respective access port. Each channel defines an inlet and an outlet and all outlets are in fluid communication with one another at a junction. And, each of the channels defines an outlet leg extending between a respective access port and the junction. The system is free from membranes proximate the access ports that would otherwise affect fluid communication between a respective channel and the chamber.

In yet another aspect, the present invention provides a method for forming a concentration gradient of an agent in a liquid by use of a membrane-free microfluidic system comprising (i) a chamber defining an interior region adapted for retaining a liquid, and (ii) a plurality of channels for housing flow of the liquid, each channel being in constant fluid communication with the interior region of the chamber via an aperture, and each channel defining an inlet portion upstream of the aperture and an outlet portion downstream of the aperture. The method comprises filling the interior region defined by the chamber with liquid. The method also comprises flowing liquid through the channels. The method further comprises administering an amount of the agent into the liquid flowing through at least one of the channels at a location upstream of the respective aperture. And, the method comprises diffusively transferring at least a portion of the agent from the flowing liquid through the aperture and into the liquid in the interior region of the chamber, whereby a concentration gradient of the agent is formed in the interior region of the chamber.

In still another aspect, the present invention provides a method for analyzing microorganisms in the presence of a concentration gradient of an agent. The method comprises providing a microfluidic system comprising (i) a chamber and (ii) a plurality of channels, each channel being in constant fluid communication with the chamber via an aperture. The method also comprises filling the chamber with liquid. The method further comprises introducing the microorganisms into the chamber. And, the method additionally comprises flowing liquid and agent through at least one of the channels whereby at least a portion of the agent is diffusively transferred through the aperture into the chamber thereby forming the concentration gradient, and enabling analysis.

In still a further aspect, the present invention provides a method for generating multiple concentration gradients within a microfluidic system. The method comprises providing a microfluidic system comprising (i) a chamber and (ii) a plurality of channels, each channel being in fluid communication with the chamber via an aperture, the microfluidic system being free of any membranes at or proximate the apertures. The method also comprises filling the chamber with liquid. The method further comprises flowing liquid through at least two of the channels. The method additionally comprises introducing a first agent into liquid flowing through a first channel whereby at least a portion of the first agent is diffusively transferred through a first aperture into the chamber thereby forming a first concentration gradient. And, the method further comprises introducing a second agent into liquid flowing through a second channel whereby at least a portion of the second agent is diffusively transferred through a second aperture into the chamber thereby forming a second concentration gradient.

In yet another aspect, the present invention also provides a method for selectively modifying a concentration gradient of an agent in a liquid within a microfluidic system over time. The method comprises providing a microfluidic system comprising (i) a chamber and (ii) a plurality of channels, each channel being in fluid communication with the chamber via an aperture, the microfluidic system being free of any membranes at or proximate the apertures. The method also comprises filling the chamber with liquid. And, the method comprises flowing liquid and agent through at least one of the channels whereby at least a portion of the agent is diffusively transferred through the aperture into the chamber thereby forming the concentration gradient. After formation of the concentration gradient, the gradient in the chamber can be selectively modified.

As will be realized, the present invention is capable of other and different embodiments and its various details are capable of modifications in numerous respects, all without departing from the invention. Accordingly, the accompanying drawings and description are to be regarded as illustrative and not restrictive.

DETAILED DESCRIPTION OF THE EMBODIMENTS

Figure 1:
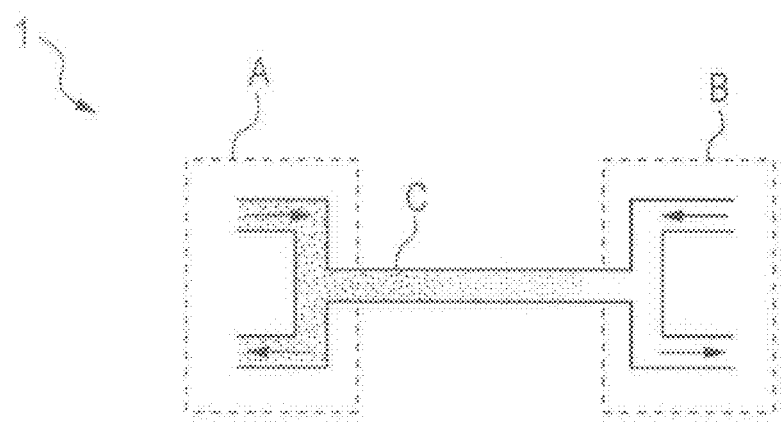
FIG. 1 is a schematic illustration of a cross channel gradient generator.

The present invention provides a microfluidic gradient generator, generally described herein as a microfluidic device, where convective flow through delivery channels is decoupled from diffusion in a main chamber without the need for membranes or gels. Several significant advantages of the device include (i) absence of shear stress in a chamber region in which one or more gradients can be formed and maintained; (ii) the device enables the generation of overlapping gradients with different spatial locations; (iii) each gradient can be addressed independently and modified dynamically; (iv) the gradient time constant is significantly less than other gradient generators using membranes or gels; and (v) chemotactic cells can be introduced in the chamber after formation of one or more gradients.

It is believed that the microfluidic devices of the present invention will facilitate progress in many diverse fields, particularly in the study of complex biological processes where cell to cell signaling plays a key role.

Before turning attention to the present invention, its various forms and preferred embodiments, it is instructive to define several terms used herein. The terms "convection" or "convective flow" as used herein refer to flow of liquid from one location to another location. The terms "diffusion" or "diffusively transferring" as used herein refer to transport or movement of one or more agents, typically dispersed, mixed, or otherwise carried by liquid, and more specifically molecules of the agent(s), that results from random molecular motion. Typically, diffusion is the net transport of molecules from a location of higher concentration to a location of lower concentration.

Another term used herein refers to a feature of the present invention microfluidic devices in which diffusion occurs from one region in a liquid to another region in the liquid without any obstructions or flow-blocking components such as flow-blocking valves. As previously noted, it is known in the prior art to position flow-blocking valves or other devices in a liquid channel such that upon establishing static liquids on all sides of the valve, the valve is then opened to create an interface between the static liquid plugs, across which diffusion can then occur. The preferred embodiment devices do not require such flow-blocking components and instead feature a unique configuration in which one or more liquid channels are in "constant fluid communication" with a chamber or other region in a microfluidic system. Hence, the term "constant fluid communication" as used herein in reference to the channels and chamber refers to absence of any flow-blocking valves that may periodically block or prevent fluid communication between locations in a microfluidic device or system.

The present invention microfluidic systems and devices provide for transport of molecules of one or more agent(s) into a chamber or other region in which the transport occurs exclusively by diffusion of the agent molecules. As explained herein, the present invention prevents transport of agent molecules by convection, such as occurring by convective flow of liquid. As previously noted, prior art strategies attempted to prevent convective flow and enable diffusion of certain molecules between two locations by placing membranes, flow-blocking valves, or gels between the locations. As previously explained, each of these strategies affects fluid communication between a respective channel and a chamber or other region of interest. The present invention decouples diffusion from convection of agent molecules without the use of membranes, flow-blocking valves, or gels. These and many other advantages and uses of the invention are described in detail herein.

Preferred Embodiment Devices

FIG. 1 schematically illustrates a one dimensional design of a cross channel gradient generator. The device 1 generally includes two convection units, designated as A and B, separated by a microchannel C that provides fluid communication between the convection units A and B. A mass balance at each convection unit A, B, or the "T" junction at each end of the microchannel C, demonstrates that matching bulk flow rates through respective inlets and outlets is a necessary condition to decouple convection through each side channel of convection units A, B from diffusion across the main channel C. If the flow at one convection unit carries a solute concentration and flow at the other convection unit carries buffer, a diffusive gradient develops across the microchannel C and remains constant as long as the flows in the convection units A and B remain constant.

Figure 2:
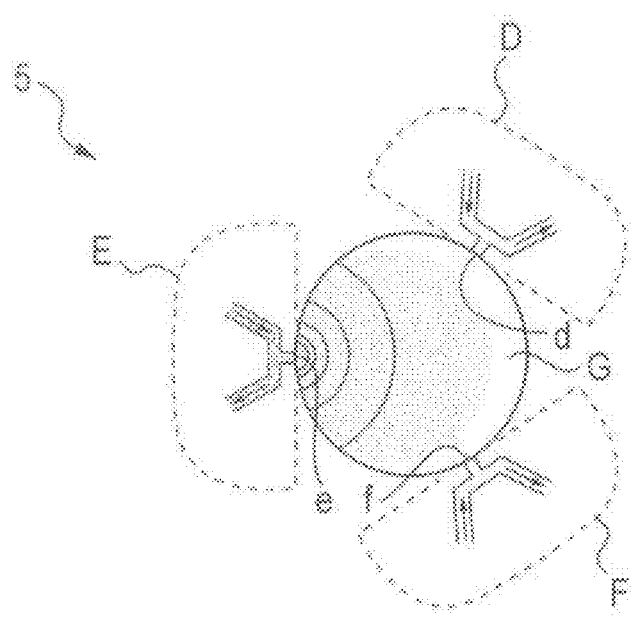
FIG. 2 is a schematic illustration of a preferred embodiment microfluidic device in accordance with the present invention.

In accordance with an aspect of the present invention, this concept is extended to a multi dimensional format in which several convection units are located about the periphery of a microchamber, preferably circular in shape, each unit functioning as a perfect sink or source for a given solute, as shown in FIG. 2. Here, the device 5 comprises a plurality of convection units, for example D, E, and F, separated by a chamber G. Each convection unit includes a channel conduit, or passage for containing and directing a liquid flowing therethrough. Respective inlets and outlets are defined for each channel in a convection unit. Each convection unit is in fluid communication with the chamber G by an access port such as ports d, e, and f shown in FIG. 2. The mass-balance condition is met indirectly by balancing the pressure between all access ports at the convection units. Thus, referring again to FIG. 2, convection or other liquid flows can be eliminated or at least significantly reduced in the chamber G by matching the pressure of the liquids at the access ports d, e, and f. Upon matching the flows (or pressures) of liquids in units D, E, and F, a concentration gradient can be formed in the chamber G by introducing a solute in the liquid flowing in convection unit E. Upon matching of the noted flows (or pressures), the solute diffuses from the convection unit E to the chamber G through the access port e.

Three aspects are important in generating stable gradients using the microfluidic devices of the present invention. First, a microfluidic chamber in the device is preferably fabricated using a rigid substrate to avoid transient flows due to compliance, deformation, or material flexure. Second, the outlets of the convection units are preferably merged through low resistance rigid channels defined in the device. And third, bubbles or other amounts of gas or vapor in the liquid are purged or otherwise reduced using a network of microchannels under reduced pressure. These aspects are all described in greater detail herein.

Generally, the preferred embodiment microfluidic device comprises (i) a microfluidic chamber where only diffusion occurs and (ii) a delivery platform provided by multiple, for example three, microchannels which deliver one or more agents or solutes using fluid flow.

Figure 3:
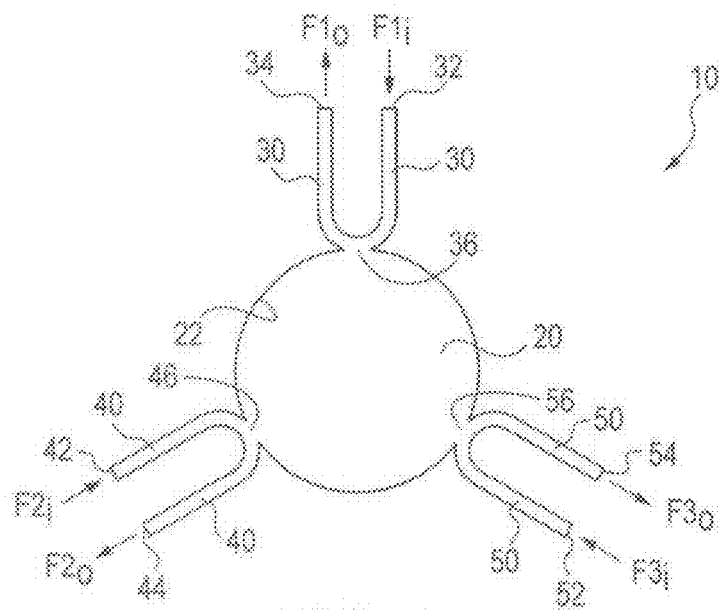
FIG. 3 is a schematic illustration of another preferred embodiment device in accordance with the present invention.

FIG. 3 schematically illustrates a preferred embodiment microfluidic device in accordance with the present invention. The device 10 includes a chamber 20 or other interior hollow region adapted for retaining a liquid. The chamber or interior region is generally defined by an interior wall 22. The device 10 also includes a plurality of channels, and preferably at least three flow channels in communication with the chamber 20. Each channel is adapted to contain and direct liquid when the liquid is flowing in the channels as described herein. The device 10 is depicted as including three channels, channels 30, 40, and 50. Channel 30 includes an inlet 32 and an outlet 34. Channel 40 includes an inlet 42 and an outlet 44. And channel 50 includes an inlet 52 and an outlet 54. Preferably, each of the channels is in fluid communication with the chamber 20 by a respective access port. Thus, channel 30 is in communication with the chamber 20 by access port 36. Channel 40 is in communication with the chamber 20 by access port 46. And, channel 50 is in communication with the chamber 20 by access port 56.

As will be appreciated, channel 30 can receive a first liquid flow F1; at the inlet 32, channel 40 can receive a second liquid flow F2; at the inlet 42, and channel 50 can receive a third liquid flow F3; at the inlet 52. Exiting liquids are designated as $F1_o$ exiting outlet 34, $F2_o$ exiting outlet 44, and $F3_o$ exiting outlet 54. The previously noted matched flow state is achieved when $F1_i=F1_o$, $F2_i=F2_o$, and $F3_i=F3_o$. At this state, no convection occurs within the chamber 20.

It will be appreciated that a significant feature associated with the present invention is that membranes are not used at or near the access ports, as is commonly practiced in the prior art. That is, membranes are not used at any of the access ports to selectively allow certain agents, solutes, or molecules to pass into the chamber from liquid in the channel. In addition, the present invention devices do not rely upon the use of flow-blocking valves. Nor do any of the devices require the use of gels in the chamber or adjacent the access ports. These are significant features of the present invention.

The access ports may be in a variety of different forms. For example, the access ports can be in the form of conduits or passageways extending between a channel and the interior of the microfluidic chamber. The access ports may also be in the form of apertures, holes, openings or the like that provide fluid communication between the interior of the chamber and a respective channel merged or otherwise formed along the chamber. Each access port may be in nearly any shape, such as circular, square, polygonal, and slit-like for example. The dimensions or size of the access ports is not critical. However, it is contemplated that for many applications, access ports having cross sectional areas of from about 0.01 mm$^2$ to about 10 mm$^2$ would be useful. Preferably, the access ports are in the form of circular apertures extending from the interior of a respective channel to the interior of the chamber.

The dimensions, shapes, and configurations of the channels and the chamber are not critical. That is, the present invention includes a wide array of devices differing in size, shape, and configuration. However, for the preferred devices described herein, it is generally contemplated that the channels are formed so as to provide a flow cross sectional area of from about 0.1 ml/min to about 10 ml/min. It will be appreciated that the present invention includes channels that are larger or smaller than the channels described herein.

The chamber in the preferred embodiment devices can be in nearly any shape and in no way is limited to the circular or cylindrical shape illustrated in the accompanying figures. For example, the chamber may exhibit a variety of different shapes. The preferred embodiment devices and their various components are sized and/or configured such that after a period of time during which liquid and agent are flowing past one or more access ports, an amount of the agent diffuses through the respective access port(s) into the chamber. Preferably, the chamber is cylindrical in shape in which the diameter is significantly greater than the height of the chamber, such as at least 10 times, more preferably at least 50 times, and more preferably at least 100 times. In this configuration, the apertures are preferably in the form of apertures or openings defined in the circumferential chamber interior wall. However, the apertures may also be formed in a planar wall of the cylindrical chamber. The chamber may also be of nearly any size. However, it is generally preferred that the size, shape, and/or configuration of the chamber is such that liquid flow through a channel is significantly easier than flow of that liquid through the chamber. Preferably, this relationship is such that resistance to flow of a liquid through the chamber is at least 1000 times greater than that for flow through a respective channel, and most preferably at least 100,000 times greater. Providing a microfluidic device with channels and chamber exhibiting this relationship serves to further minimize and significantly reduce the potential for convective liquid flows in the chamber.

The preferred embodiment microfluidic devices may also utilize one or more flow controllers for governing and/or controlling the rate of flow of liquid in each of the channels. As will be appreciated by those skilled in the art, a flow controller may be in a variety of different forms and configurations. The flow controller can include one or more pumps adapted for microfluidic applications. The pump operation can be controlled to selectively adjust the flow rate of liquid that the pump is displacing. Alternatively, or in addition, the flow controller can be in the form of one or more flow controlling devices such as in-line valves that control the rate and/or volume of liquid passing therethrough. As noted, a wide array of system configurations and components can be used as one or more flow controllers. For example, it is contemplated that one or more flow controllers may be in the form of a pump or other liquid displacement device that moves liquid in the various channels and past corresponding access ports and a chamber. The channels may constitute a closed loop system. Thus, liquid in a loop can recirculate and diffuse solutes out through the access port(s), but the liquid does not leave the channels. Specifically for example, it is contemplated that a system may utilize a closed loop conduit for each channel, which is in fluid communication with a chamber via an access port as described herein. For a system having three channels; three separate loops, each in communication with the chamber via a respective access port, is provided. A pump may be provided for each loop to displace liquid in the loop. Thus, the multiple pumps would constitute flow controllers. In addition to pumps, other liquid displacement devices are contemplated for use as a flow controller. For example, a syringe or other like device could be used to displace liquid within a system and particularly, channels.

Control of the liquid flows may in certain applications be optionally accomplished by use of an electronic processor. Sensors, such as in the form of pressure or flow transducers, can be used to provide information, i.e. signals, to an electronic processor. Control algorithms executed by the processor can be used to operate one or more of the flow controller devices described herein to achieve a desired flow rate at desired location(s) in the system.

During a preferred operation of the device 10 depicted in FIG. 3, a suitable liquid, examples of which are described in greater detail herein, fills the chamber 20 and is flowing in each of the channels 30, 40, and 50. In accordance with the present invention, the flow rate of the liquid is matched in each of the channels which results in a condition in which no convective flows occur within the chamber. As previously noted, the flow rates are matched when $F1_i=F1_o$, $F2_i=F2_o$, and $F3_i=F3_o$. Pressures are matched when the pressures as measured at access ports 36, 46, and 56 are all the same or very nearly the same. Specifically, if the liquid flow rates (or pressures) in each channel 30, 40, and 50, are identical, as measured at access ports 36, 46, and 56, no flows of the liquid will occur through the access ports. However, as explained in greater detail herein, any solutes, agents, or other materials carried by the liquid(s) flowing through the channels 30, 40, and 50, may pass through one or more of access ports 36, 46, and 56 and enter the chamber 20. This transport through one or more of the access ports is exclusively by diffusion.

As noted, it is important in the practice of the present invention to match flow rates (or pressures) as measured at each of the access ports. Although exact matching is most preferred, it will be understood that for most if not all applications, exact matching is not feasible. Thus, it is contemplated that matching of flow rates (or pressures) within 98% of one another may be appropriate for many applications, with 99% being preferred, and 99.5% more preferred, 99.9% more preferred, and 99.999% being even more preferred. For example, it is preferred that the values for $F1_i$ and $F1_o$ be within 99.5% of one another, that $F2_i$ and $F2_o$ be within 99.5% of one another, and that $F3_i$ and $Fe_o$ be within 99.5% of one another. Regarding pressures, it is preferred that the pressures as measured at access ports 36, 46, and 56 be within 99.5% of one another. Thus, the terms "matching" or "match" are used herein to refer to these extents to which flow rates (or pressures) of liquids in the channels, are the same or very nearly the same.

Referring further to FIG. 3, a preferred operation of the device 10 is achieved by filling the chamber 20 and channels 30, 40, and 50, with one or more liquids. Preferably, the same liquid is used for the channels and for filling the chamber. However, the present invention includes the use of different liquids. Flow of liquid is initiated through each of the channels. Optionally, one or more sensors (not shown) preferably provide information as to the rate of flow through each of the channels, and preferably at each of the access ports 36, 46, and 56. One or more flow controllers (not shown) are operated so that the rate of flow of liquid through each of the channels is the same, or at least very nearly so. As explained in greater detail herein, if the various liquid flows in the channels are matched, then no liquid flows, i.e. convection, will occur between the channel(s) and the chamber. Any agents, solutes, or other materials in the liquids flowing through the channels 30, 40, and 50 may however, pass through a corresponding access port by diffusion.

Figure 4:
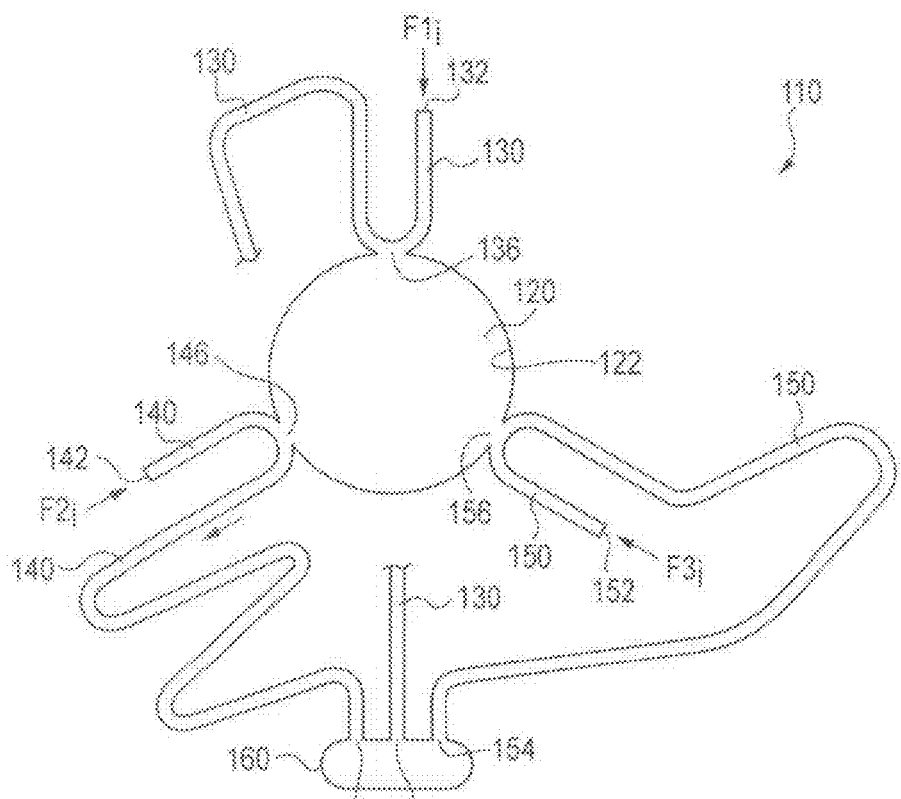
FIG. 4 is a schematic illustration of yet another preferred embodiment device in accordance with the present invention.

FIG. 4 schematically illustrates another preferred embodiment device 110 in accordance with the present invention. The device 110 utilizes a unique pressure-balancing configuration between the outlet ends of the channels which enables matching of flows in the channels without having to monitor and control such liquid flows, as in the device of FIG. 3. And thus, so long as a flow of liquid may be uniformly administered at each of the channel inlets, it will generally not be necessary to use any controllers or related sensors to adjust or control flow in the channels. The device 110 shown in FIG. 4 is similar to the previously described device 10 and includes a chamber 120 generally defined by an interior chamber wall 122. The device 110 also includes a plurality of channels, and preferably at least three flow channels 130, 140, and 150. Channel 130 includes an inlet 132 and an outlet 134. Channel 140 includes an inlet 142 and an outlet 144. And, channel 150 includes an inlet 152 and an outlet 154. Each of the channels is in fluid communication with the chamber 120 by a respective access port 136, 146, and 156. And, each of the outlets 134, 144, and 154 are in communication with one another at a junction 160, for example.

The device 110 features a pressure-balancing configuration in which each of the outlets of the channels are in fluid communication with each other, and thus are at the same pressure as one another. In addition, this pressure-balancing configuration also requires that the pressure differential or pressure drop as measured between an access port and a respective outlet, is the same. This ensures that the pressure of the liquid at each access port is the same, or at least very nearly so. Specifically, with reference to FIG. 4, it is preferred that (i) the pressure differential taken across the channel 130 between the access port 136 and the outlet 134; (ii) the pressure differential taken across the channel 140 between the access port 146 and the outlet 144; and (iii) the pressure differential taken across the channel 150 between the access port 156 and the outlet 154; are all the same, or at least very nearly so. It is preferred that these pressure differentials are all matched as that term is used herein. A convenient strategy to ensure that these pressure differentials are all matched is to form each of the outlet legs, i.e. the portion of a channel extending between an access port and the junction at which the outlets are all in fluid communication, so that the legs all have the same length and exhibit the same resistance to flow. This typically necessitates that the interior passageway defined in or constituting each of the channels has a uniform size and configuration across the entire length of each outlet leg. Thus, referring to FIG. 4, preferably, the distances of (i) the outlet leg from the access port 136 to the outlet 134, (ii) the outlet leg from the access port 146 to the outlet 144, and (iii) the outlet leg from the access port 156 to the outlet 154, are all the same, or very nearly so.

Figure 5:
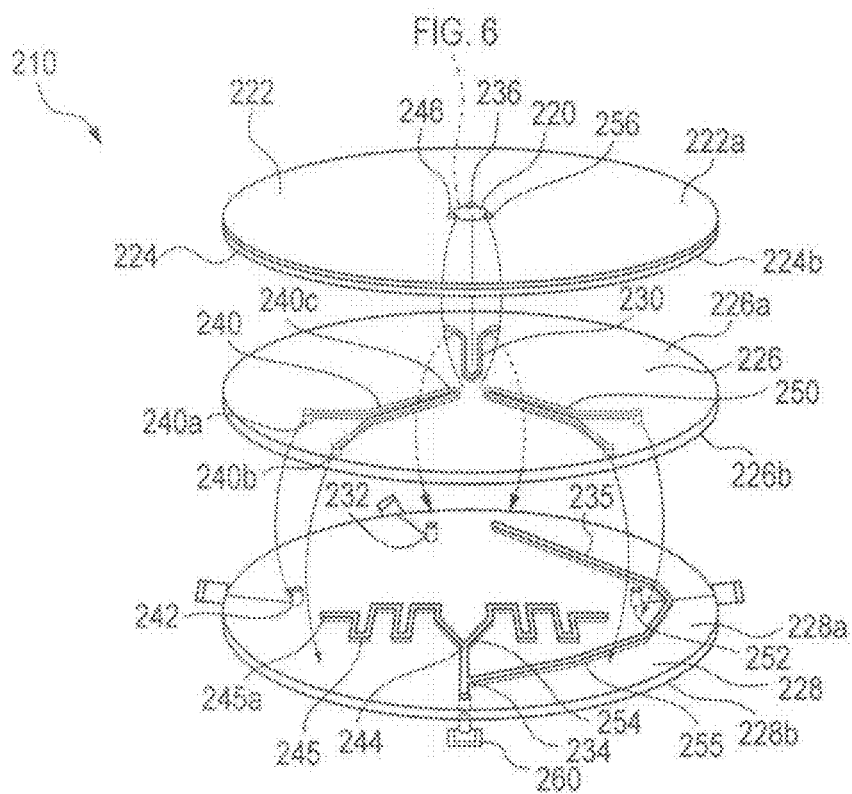
FIG. 5 is an exploded view of still another preferred embodiment microfluidic device.
Figure 6:
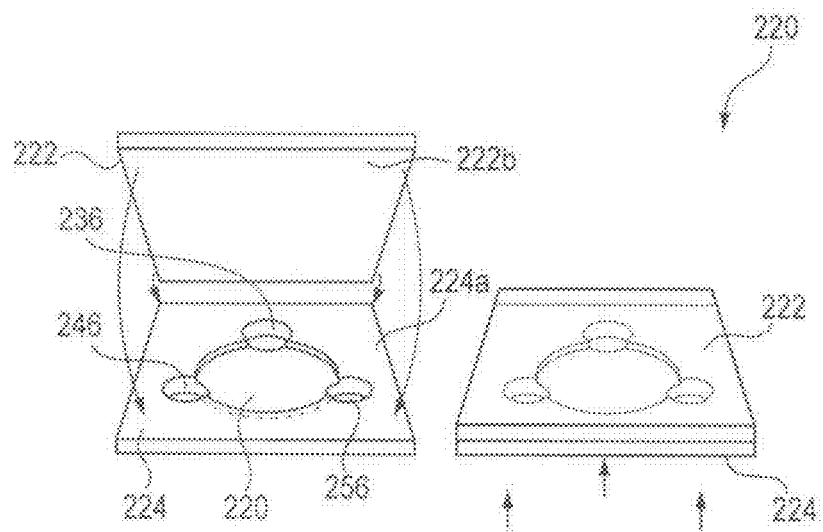
FIG. 6 is a detailed view of a chamber of the device illustrated in FIG. 5.

FIG. 5 illustrates yet another preferred embodiment device 210 in accordance with the present invention. The device 210 comprises a chamber 220 and a plurality of channels such as channels 230, 240, and 250. Associated with each channel is an outlet leg, such as legs 235, 245, and 255. Each channel is in fluid communication with the chamber 220 via an access port, such as ports 236, 246, and 256, as shown in FIGS. 5 and 6. Corresponding outlet legs extend between the access ports and a junction 260 at which outlets of each channel merge with one another. Each channel also defines corresponding inlets and outlets. Channel 230 defines an inlet 232 and an outlet 234. Channel 240 defines an inlet 242 and an outlet 244. And, channel 250 defines an inlet 252 and an outlet 254. Outlet leg 235 extends from the access port 236 to the outlet 234. Outlet leg 245 extends from the access port 246 to the outlet 244. And, outlet leg 255 extends from the access port 256 to the outlet 254.

Although the preferred embodiment device 210 can be formed in an array of different configurations, the exploded views of FIGS. 5 and 6 illustrate a preferred assembly. Preferably, the device 210 is formed as a layered array of glass and polymeric layers. The chamber 220 is preferably defined and formed between two glass layers such as a first outer glass layer 222 and a second glass layer 224 that is immediately adjacent the outer layer 222. The glass layer 222 defines an upwardly directed face 222a and a downwardly directed face 222b. And, the glass layer 224 defines an upwardly directed face 224a and a downwardly directed face 224b. As best shown in FIG. 6, the chamber 220 is partially defined in the glass layer 224. Specifically, the chamber 220 is formed as a recessed region along the upwardly directed face 224a of the glass layer 224. Upon placement of the glass layer 222 thereon, i.e. contacting downwardly directed face 222b with the upwardly directed face 224a, the chamber 220 results. The access ports 236, 246, and 256 are also preferably defined in the glass layer 224, and as shown in FIG. 6, extend through the thickness of the glass layer 224. Each access port also extends into, and thus provides communication with, the chamber 220. The device and its various components, e.g. the chamber, can be formed from a wide range of sufficiently rigid materials such as various glasses, ceramics, plastics, quartz, minerals, silicon, sapphire, metals, and combinations thereof. It will be appreciated that the present invention includes other configurations and assembly practices. A wide array of potential applications and materials are contemplated. For example, the present invention could potentially be used in studies involving materials such as hydroapatite (also known as hydroxyapatite), which is the main component of bone. In such contemplated studies, bone or dental environments could be simulated.

The channels 230, 240 and 250, their corresponding inlets and outlets, and their outlet legs, are preferably provided by a delivery platform conveniently formed by two polymeric layers assembled in an overlying manner in like fashion as the previously described glass layers forming the chamber 220. Preferably, the delivery platform is formed from a first polymeric layer 226 and a second polymeric layer 228 disposed under the first layer 226. The first layer 226 defines an upwardly directed face 226a and an oppositely directed, i.e. downwardly directed, face 226b. And, the second layer 228 defines an upwardly directed face 228a and a downwardly directed face 228b. It will be understood that the references to upwardly and downwardly for the various glass and polymeric layers are merely for purposes of description and in no way limit the orientation, use, or configuration of the device 210.

The channels 230, 240, and 250 are preferably defined in the first layer 226 and preferably along the upwardly directed face 226a. The outlet legs 235, 245, and 255 are preferably defined in the second layer 228 and preferably along the upwardly directed face 228a. Also defined in the second layer 228 are apertures that constitute the inlets 232, 242, and 252 for each of the channels. Each of the channels 230, 240, and 250 is configured and formed in the first layer 226 such that the channel extends between two apertures extending through the thickness of the layer 226 and a location on the face 226a corresponding to the location of an access port defined in the glass layer 224 and accessible from the face 224b of that layer. Thus, for channel 240 for example, that channel extends between apertures 240a and 240b and a location 240c which, upon positioning of the layers 224 and 226 together, provides communication with the access port 246. It will be appreciated that the invention includes other configurations for the channels.

The second polymeric layer 228 preferably defines apertures which serve as inlets to each of the channels. These apertures are preferably located such that upon positioning of the layers 224 and 226, a corresponding aperture in the layer 226 is aligned with one of the apertures providing access to a respective channel. For example, the aperture constituting inlet 242 in the second layer 228 is aligned with the aperture 240a in the first layer 226. And, the outlet legs defined in the second layer 228 are also configured such that each extends between a first location that is aligned with one of the previously described channel apertures. Thus, for outlet leg 245 defined in the second layer 228 for example, that outlet leg extends between outlet 244 and location 245a which is aligned with aperture 240b defined in the first layer 226. It will be understood that the invention includes other arrangements and configurations for the outlet legs and associated apertures.

Thus, in the assembled device 210, the flow path of a liquid flowing through the channel 240 is as follows. The liquid enters the device 210 from the underside of the layer 228, i.e. face 228b, through inlet 242, and passes through the second layer 228. The liquid then passes through the first layer 226 through aperture 240a and enters the channel 240 defined along the upwardly directed face 226a of the layer 226. The liquid flows through that channel past the access port 246 and then flows through the aperture 240b, through the first layer 226, and then enters the outlet leg 245 defined in the upwardly directed face 228a of the second polymeric layer 228. Upon entering the outlet leg 245, at location 245a, the liquid flows through that channel to its outlet 244. As with the previously described device 110, it is preferred that the outlets of all channels are in communication with one another, and so the liquid exiting the outlet 244 may then be combined with liquid leaving the other channels or be directed to a common outlet such as a junction 260.

As previously explained with regard to the device 110, it is desirable to form each of the outlet legs 235, 245, and 255, such that each has the same length and/or equal resistance to flow. As previously noted, it is also desirable that each channel has the same interior span. When merging liquid flows in similarly sized channels to a common outlet located along the periphery of the device, the various shapes for the outlet legs shown in FIG. 5 will be appreciated. That is, the legs may be in a variety of shapes so long as they all have the same length.

In the preferred embodiment device 210 described herein, the microfluidic chamber 220 is preferably about 1.5 mm in diameter and from about 3 to about 20 μm thick, and as previously noted, is preferably fabricated in glass to avoid compliance, i.e. dimensional distortion. The chamber 220 can be etched on a glass wafer, i.e. the layer 224, and a plurality of through-holes drilled or otherwise formed to allow the delivery and removal of solutes or other agents carried by liquids flowing through the channels. A second glass wafer, i.e. the layer 222, is placed on top of the other glass wafer to enclose the chamber. In the illustrated preferred configuration, the chamber is circular with three radially distributed access ports, each 1 mm in diameter and 500 μm deep, serving as sources and sinks for the delivery and removal of solutes or other agents into the chamber. Preferably, each access port is equidistant from the other access ports.

The delivery platform is preferably formed by a rigid plastic layer for the bottom layer 228, such as PMMA, preferably from about 6 to about 12 mm in thickness, and an elastomeric layer for the top layer 226, such as polydimethyl siloxane (PDMS) used as a sealing or gasket layer between the rigid plastic layer, i.e. layer 228, and the glass microfluidic chamber, see FIG. 5. Poly(methyl methacrylate) (PMMA) or poly(methyl 2-methylpropenoate) is a thermoplastic and transparent plastic. Chemically, it is the synthetic polymer of methyl methacrylate. This material is available under various tradenames such as Plexiglas, Vitroflex, Limacryl, R-Cast, Per-Clax, Perspex, Plazcryl, Acrylex, Acrylite, Acrylplast, Altuglas, Polycast, Oroglass and Lucite and is commonly called acrylic glass or simply acrylic. The PDMS layer, i.e. layer 226, with channels directed upwards, is aligned with the access ports and bonded, preferably non-permanently, with the glass wafer defining the underside of the chamber. The three microchannels that result along the interface between the sealing layer and glass layers, are connected through the access ports and the microfluidic chamber. Apertures or holes at both ends of each microchannel are used to provide communication with the corresponding features in the PMMA layer. The PMMA layer may include syringe needles glued or otherwise affixed on the backside (or other communication inlets) and channels milled on the front side to interface the needles with the apertures in the sealing (PDMS) layer. While all gasket inlets are independent, as previously explained, the outlets are preferably connected through rigid milled channels, such as 1 mm deep by 1 mm wide, and merged into a common outlet.

Due to differences in height, the resistance to flow through the microfluidic chamber 220 is approximately 10,000 times greater than the resistance to flow through the rigid channels. Delivery of liquids is preferably performed with external syringe pumps with matched flow rates. As noted, the resistance of all rigid channels from the access ports to the common outlet is also matched by forming each channel to have the same length as the other channels, to ensure pressure at the access ports is balanced. This practice results in no convection in the chamber, only diffusion if the flows delivered by the syringe pumps are matched at all times. Therefore, if all the flow rates are modified simultaneously and in the same proportion, the pressure balance is maintained.

Figure 7:
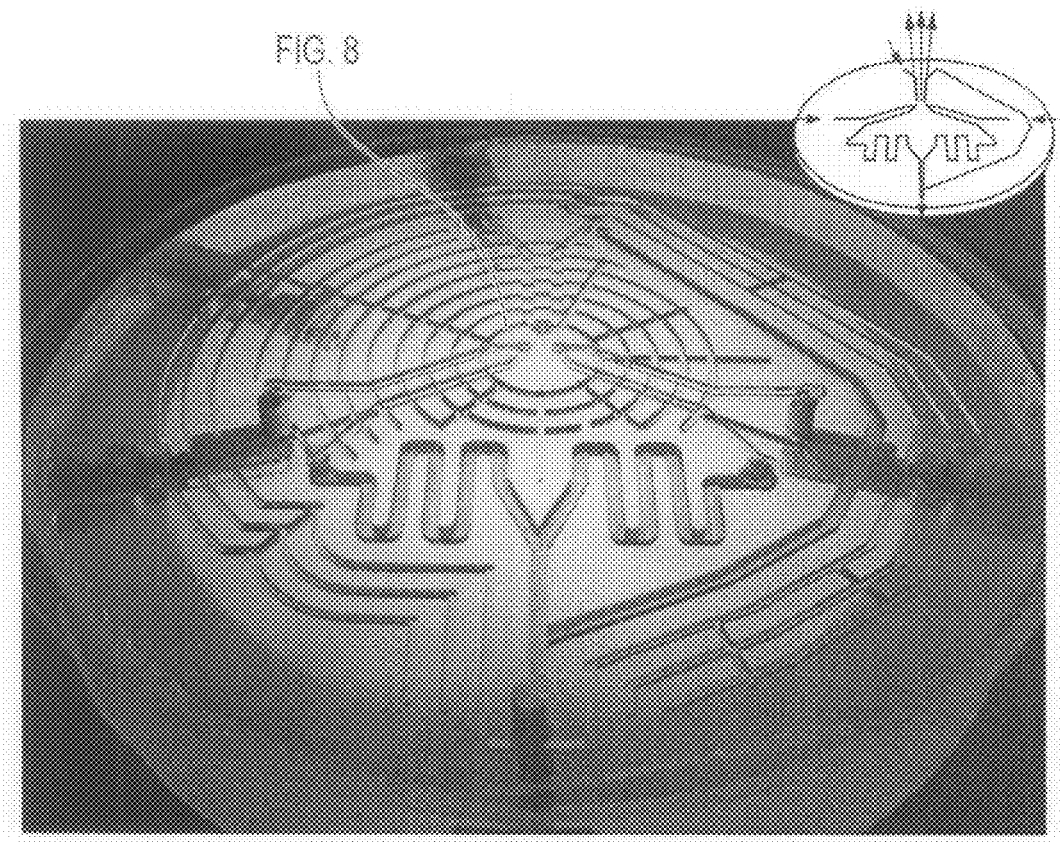
FIG. 7 is a photograph of another preferred embodiment microfluidic device in accordance with the present invention.
Figure 8:
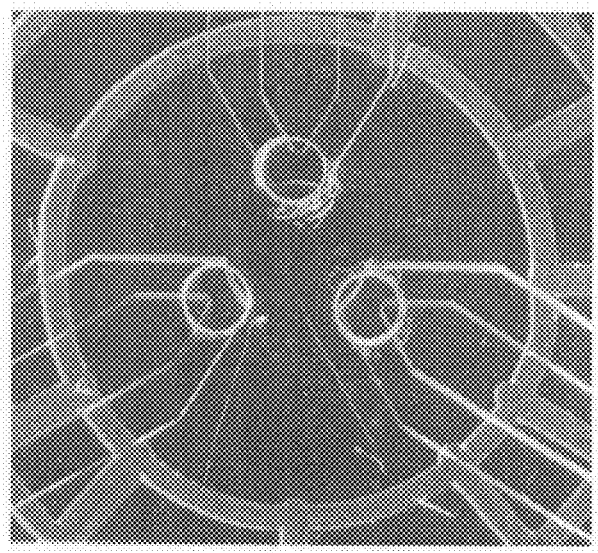
FIG. 8 is a detailed view of a chamber of the device illustrated in FIG. 7

FIGS. 7 and 8 are photographs of the delivery platform portion and the chamber portion of another preferred embodiment device similar to the previously described device 210. Referring to those photographs, the plastic or bottom layer also preferably includes a network of milled channels along an upwardly directed face of that layer. Vacuum or other reduced pressure applied to the network results in a distribution of negative pressure between the plastic layer and the sealing layer. Early attempts in designing microfluidic devices failed to generate stable gradients because of bubble formation inside the delivery channels that modified the resistance of the channels and the pressure balance at the access ports. The vacuum network as described herein, in addition to retaining the plastic and the sealing layer together, also purges bubbles from the liquid generated during priming of the device.

Device Operation

The illustration in FIG. 7 shows three fluid paths through the delivery platform of the device 210. In a typical operation, liquid introduced with an external syringe pump through an inlet flows through a channel defined in the sealing layer, past the corresponding access port, and back into the channel or more specifically an outlet leg thereof, defined in the plastic layer where the liquid merges with fluid coming from the other branches into a common outlet. While no bulk fluid flow occurs through the access ports, because the pressure is balanced among them, solute can be transferred between the access ports through the microfluidic device by diffusion.

Prior to use of the preferred embodiment device, the microfluidic chamber is prefilled with a liquid buffer. The device is assembled, vacuum is applied to the vacuum network, and buffer liquid is introduced through the three inlets with syringe pumps, typically about 1 ml/min, until the buffer flows through the three delivery channels, past the common outlet and reaches a waste container. Pumps are turned off and the device held stationary for approximately 30 minutes to purge any bubbles that may exist or otherwise form in the system.

A typical operation starts after the microfluidic device is prefilled with buffer and syringe pumps turned off. Valve(s) are preferably used to prevent fluidic communication between syringes and the microfluidic device. A syringe with buffer is replaced with a syringe containing a solute or agent, e.g. fluorescein or bacteria, and the three syringe pumps are turned on with matched high flow rates, approximately 2 ml/h to 10 ml/h, to expedite the exposure of the access ports to the solutes, for approximately 1 minute. Subsequently, all the flow rates are reduced to, for example approximately 0.01 ml/h to 0.1 ml/h, to maintain the concentrations at the access ports while limiting reagent consumption.

Liquids and Agents

The present invention microfluidic systems and devices can be used with a wide array of liquids and agents. Nearly any type of liquid can be used for flowing in the channels. Any flowable, noncompressible material, i.e. a liquid, can be used. It will be appreciated that typically caustic or otherwise corrosive liquids; toxic; and/or flammable liquids are generally not preferred. However, the present invention includes the use of such liquids if adequate measures such as appropriate safety precautions are adopted. Several characteristics of preferred liquids for use in the present invention systems and devices are as follows.

It is generally preferred that the liquid remain in a liquid state over the entire temperature range at which the system or device is used. That is, liquids having freezing or boiling points within the expected temperature range at which the device is used, are undesirable. It is also desirable that liquids having relatively constant viscosities over the expected range of temperatures and flow rates, are preferred.

Although it is contemplated that a single liquid or rather, a single material in liquid form, will be used throughout the present invention system and devices, i.e. in the channels and in the chamber; it is contemplated that multiple liquids may be used. For example, the present invention includes the use of a first liquid in the chamber and a second liquid in the channels. The invention also includes the use of multiple liquids in the chamber and/or in the channels, and different liquids in the chamber and/or in the channels.

The wide range of liquids that may be used in the preferred embodiment systems and devices may be characterized in terms of their viscosity, and specifically their dynamic viscosity. Generally, liquids having viscosities of from about 0.1 cP to about 100,000 cP and more typically from about 0.5 cP to about 10,000 cP may be used. These liquids are distinguishable from gels which typically exhibit viscosities greater than 100,000 cP. As previously noted herein, prior art devices are known which utilize gel materials in chamber regions or access regions to such chambers to prevent convective flows yet permit diffusive transport, e.g. through the gel. A significant feature of the present invention is the provision of a microfluidic system as described herein which is free from gels, and particularly free from hydrogels. That is, in a preferred embodiment, the microfluidic system of the present invention is free from either or both membranes and gels. The term "gel" as used herein refers to gel materials having viscosities greater than 100,000 cP.

Preferably, the agents that are carried by or otherwise mixed with the liquid and which are diffusively transferred into the chamber are generally in the form of materials that are soluble in the liquid. However, it is contemplated that the agent material could be insoluble so long as it was appropriately sized such that particles or other amounts of the agent can pass through the access port(s) and into the chamber during operation of the device. That is, the present invention is not limited to the use of agents that are soluble in the liquid.

Examples of agents include, but are not limited to, chemical compounds, pharmaceutical compounds, particulate matter, nanoparticles and generally any material different than the liquid within which the agent is carried or dispersed. Agents may also include a wide array of biological agents and/or materials such as, but not limited to, for example various biomolecules, e.g. lipids, proteins, polypeptides, nucleic acids, saccharides, and the like. Agents may also include a diverse array of microorganisms such as, but not limited to, for example prokaryotes such as bacteria, eukaryotes such as protists, animals, fungi, plants, and viruses and the like.

Furthermore, the present invention includes the use of multiple agents. Using multiple agents allows multiple concentration gradients to be formed in the microfluidic system or device. Generally, the one or more agents are selected such that the agents are compatible with the liquids, do not react with the liquids, are preferably soluble or at least miscible in the liquids, and also exhibit stable and relatively uniform properties over the temperature range of interest.

Gradient Generation

The gradients referred to herein are concentration gradients of one or more agents in a liquid. The gradients are typically formed in the chamber or other interior region of the microfluidic systems and devices described herein. Although it is contemplated that the gradients will be regions of varying concentration of agent(s) in liquid, it is contemplated that the invention can be used to form and/or analyze other types of gradients in the liquids. For example, formation of other gradients is contemplated such as density gradients, charge gradients, color gradients, and the like.

The time constant of a gradient generator for a given chemical is a measure of how fast the chemical gradient reaches steady state after the concentrations between source and sink are modified. The time constant and therefore, the time required to reach steady state, is independent of the final value of the gradient.

Figure 9:
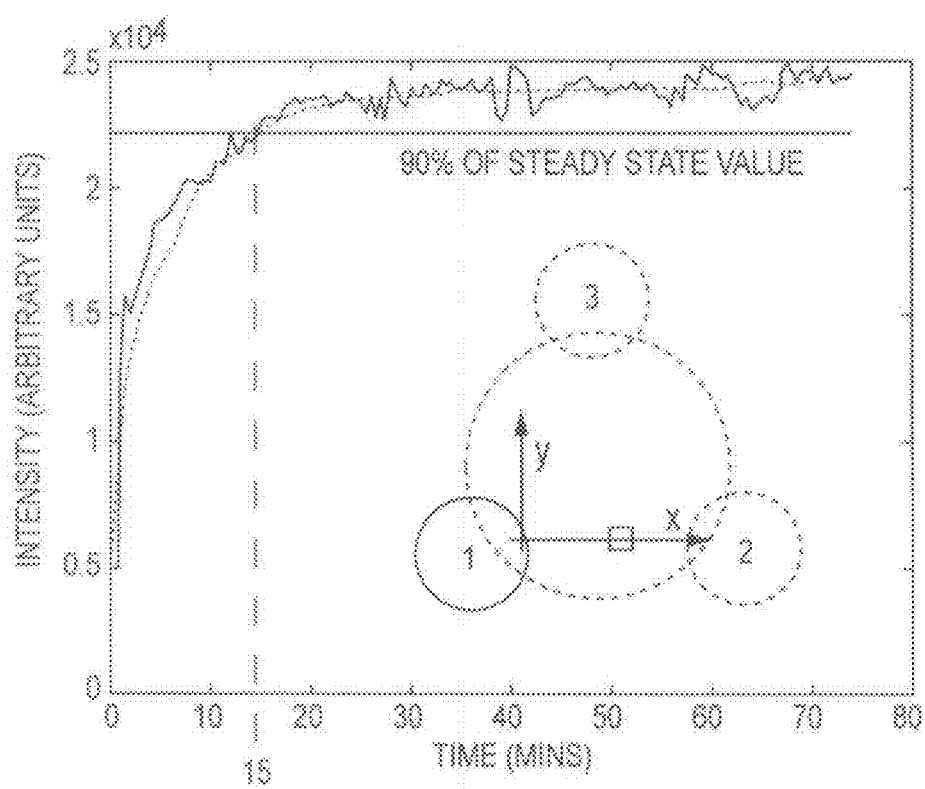
FIG. 9 is a graph of intensity of light measured at a single evaluation point in a chamber of a preferred device, over a period of time.

To determine empirically the time constant of a preferred embodiment microfluidic device, the device was prefilled with buffer as described previously, and at a given time, a solution of carboxyfluorescein (1 mmol) was introduced through access port 1, as shown in FIG. 9. The change in intensity at a single location between access port 1 and access port 2, was monitored as shown in FIG. 9. The plot of FIG. 9 is believed to be indicative of the temporal evolution at all locations in the gradient. Flow rates were held constant throughout the investigation to maintain the concentrations constant at the access ports. The monitored intensity reached 90% of its steady state value in 15 minutes, which is approximately one order of magnitude faster than gradient generators using membranes or gels in similar conditions, which typically are on the order of hours. With this value, the time constant of the gradient generator for small molecules was calculated as $\tau=t_{90\%}/2.4=6.5$ minutes.

The time constant of a system may also be estimated using a one-dimensional approximation. The temporal evolution of a chemical gradient between two infinite parallel planes where one (1) is a perfect source or perfect sink is given by equation (1) as follows:

$$C = C_0\left(1 - \frac{x}{l} - \frac{2}{\pi}\sum_{n=1}^{\infty} \frac{\sin\left(\frac{n\pi x}{l}\right)}{n} \cdot e^{-\frac{D^2\pi^2}{l^2}t}\right) \quad (1)$$

where C is the concentration at any position x between the two planes at a time t, $C_0$ is the source, l is the distance between the planes, and D is the diffusion coefficient of the molecules. The time constant of the gradient is determined by the exponential term of the infinite numerical series. The time constant for the first harmonic (n=1) of the series can be calculated by equation (2) as follows:

$$t = \frac{\pi^2 D}{l^2} \quad (2)$$

In this case, $\tau=7.6$ min (D=$5\cdot10^{-10}$ m$^2$/s; l=$1.5\cdot10^{-3}$ m). This result is in close agreement with the estimated value, and supports the use of equation (2) as a first approach to predict gradient dynamics. In this case, the ratio between size of the access ports and distance between them is close to one, and the 1-dimension approximation holds. Fast transient times should be relevant in dynamic experiments, e.g. evaluation of the time scale of a cellular response to a soluble signal. In general, the time scale of the gradient generation should be significantly smaller than the time scale of cellular response to decouple the dynamics of the two systems.

A unique feature of the preferred embodiment microfluidic devices, systems, and methods, as compared to many of those of the prior art, is that diffusion into a chamber or other region of interest occurs at least in part as a result of flow of liquid in one or more channels, past respective access ports. This feature results in a continuously renewed concentration of agent on the channel side of a respective access port. And, diffusion can be controlled by controlling flow of liquids in the channels. In contrast, many prior art strategies relied upon static liquid volumes containing agent which only upon being exposed to other liquids of different concentrations or free of agent, then form gradients.

Gradient Maintenance

Gradients generated in the microfluidic chamber are steady as long as the concentrations in the access ports remain constant. A diffusive flux maintains the gradient static at the expense of depleting molecules from the source and accumulating them in the sink. The access ports can either be flushed with constant flow rate liquid to maintain their concentration at all times, or they can be flushed with liquid at given intervals to reset concentrations after such concentrations decay below a threshold. In both cases, the diffusive flow between source and sink is governed in one dimension by the first of Fick's laws; which is shown below as equation (3):

$$J = -D\frac{\partial C}{\partial x} = -D\frac{C_1 - C_0}{l} \quad (3)$$

where J is diffusive flux, l the distance between source and sink, and $C_1$ concentration at the source and $C_0$ concentration at the sink. The product of the diffusive flow multiplied by the area across which diffusion takes place, yields the mass transport of molecules between source and sink.

The time required for a steady gradient to decay 10% when the flows are stopped and the concentration of agents at the access ports are no longer replenished was measured and found to be t=1.46 h. Therefore, turning on the fluid flow through the delivery channels for approximately 1 minute every 90 minutes ensures that the concentration gradient is maintained always within 10% of its steady state value. An estimation using equation (1) and equation (2) (1 dimensional approximation) yielded t=3.46 h.

Replenishing the access ports only at given intervals allows for time periods in which no flow is necessary, and where pumps can be turned off and syringes replaced without disturbance of gradients in the chamber. Since the estimation and empirical value are on the same order of magnitude, similar simple calculations can be used to guide the design concerning the function of the external pumps.

Overlapping Diffusive Gradients

Figure 10:
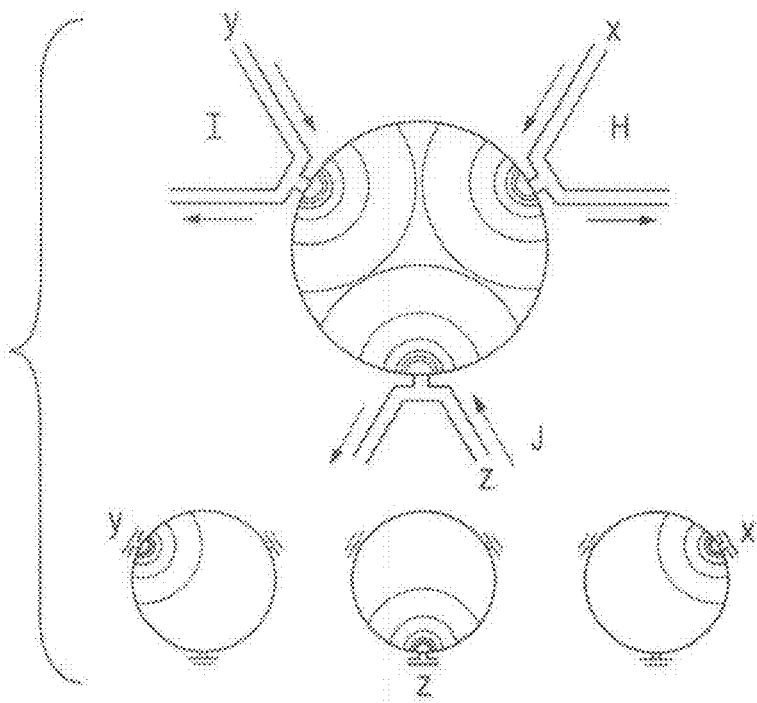
FIG. 10 is a schematic illustration depicting overlapping diffusive gradients formed in a chamber of the preferred device, as the location of a source agent changes.
Figure 11:
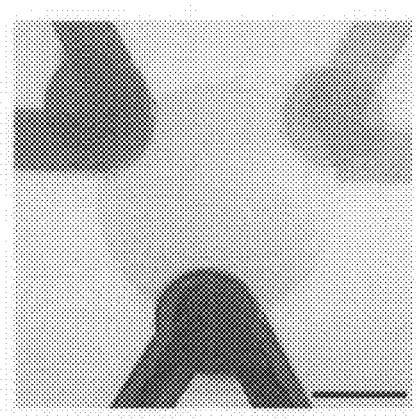
FIG. 11 is a photograph of overlapping dye gradients in a chamber of the preferred device.

Chemical gradients with different spatial location(s) can be overlapped and maintained constant using the preferred embodiment microfluidic device. For example, referring to FIG. 10, three different primary color dyes x, y, and z were introduced in a microfluidic chamber of a preferred embodiment device, each dye delivered through a different convection unit, H, I and J as shown in the top portion of FIG. 10. A concentration gradient formed for each of the dyes across the chamber, as seen in FIG. 10 bottom, produces what may best be considered as a palette of overlapping colors as shown in FIG. 11.

The geometry of the microfluidic chamber governs, at least in part, the steady state distribution of agent concentration. Thus, the overlapping gradients can be customized or otherwise tailored with modifications to the shape of the chamber and the position and size of the access ports.

Each specific location inside the microfluidic device has a distinct steady state concentration of agent or solute, indicating that a combination of agents or solutes is different at any other location and is maintained constant over time. In the example depicted in FIG. 10 where three different primary color dyes are introduced into respective access ports, the resulting gradients that form in the chamber may be analogous to an artist's color palette having numerous combinations of colors resulting from mixtures of the three primary colors, wherein each combination or mixture is different at various locations on the palette. Similarly, it is possible to generate a predictable array of concentrations of different chemicals provided they do not interact. This would allow, for example, to culture cells in the chamber and expose them to a number of drugs distributed in a continuous blend of relative concentrations.

Spatiotemporal Control Over Diffusive Gradients

To demonstrate spatiotemporal control (i.e. location-based control and/or time-based control) using the preferred embodiment microfluidic device, a diffusion gradient was created inside a circular chamber and its angular position modified over time until the gradient was fully rotated around its center. The concept is somewhat analogous to the working principle of AC electrical motors where coils in the stator are sequentially activated to generate a magnetic field that rotates around its center, see FIGS. 12 and 13 in this regard.

Figure 12:
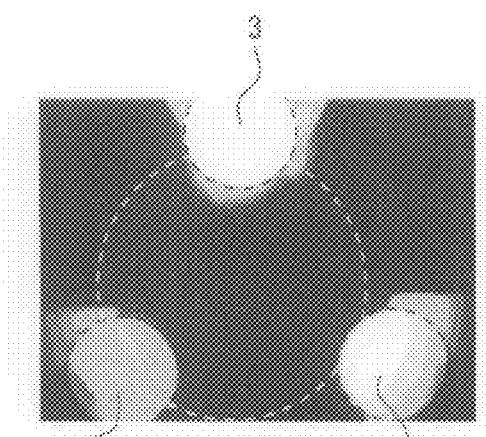
FIG. 12 is a photograph of a chamber of a preferred device.
Figure 13:
FIG. 13 is a schematic illustration of an actuation sequence in which the angular position of a source agent changes, thereby altering a diffusion gradient over time.

After pre-filling the microfluidic device with buffer, a 1 mmol solution of carboxyfluorescein was introduced through access port 1 shown in FIG. 12, buffer through access ports 2 and 3, and a gradient was allowed to develop for 15 minutes (0.1 ml/h flow rates). Subsequently, the syringe pumps were stopped, valve(s) were closed between syringes and the device, syringes were switched to introduce buffer through access ports 1 and 3, and the fluorescein through access port 2. Then, the valve(s) were opened and the syringe pumps were activated. This operation was repeated several times to cycle the introduction of fluorescein through each port as shown in FIG. 13. The gradient reached quasi steady-state in about 15 minutes. The sequence had three steps, therefore the minimum time needed to perform a full rotation was about 45 minutes.

Figure 14:
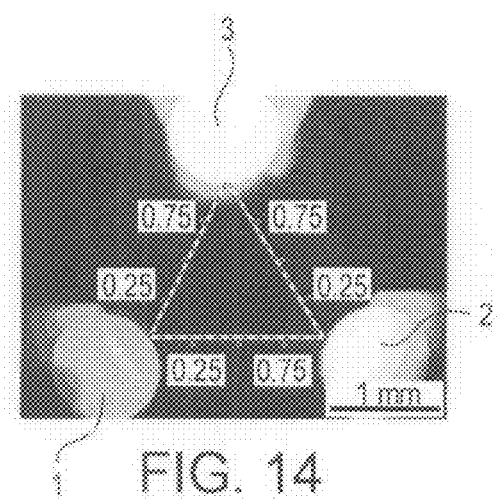
FIG. 14 is a photograph of the chamber of FIG. 12 depicting lines between access ports, along which scans were conducted.
Figure 15:
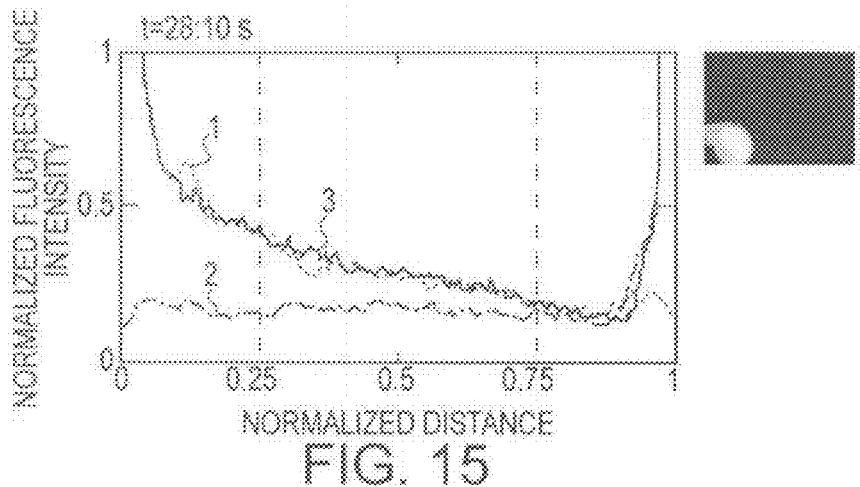
FIG. 15 is a graph of light intensity after a particular period of time as measured along the lines referenced in FIG. 14.
Figure 16:
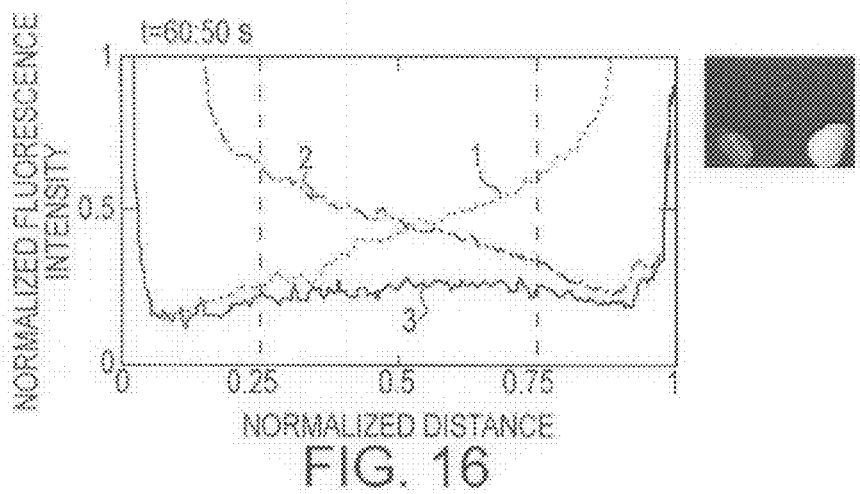
FIG. 16 is a graph of light intensity after another period of time as measured along the lines referenced in FIG. 14.
Figure 17:
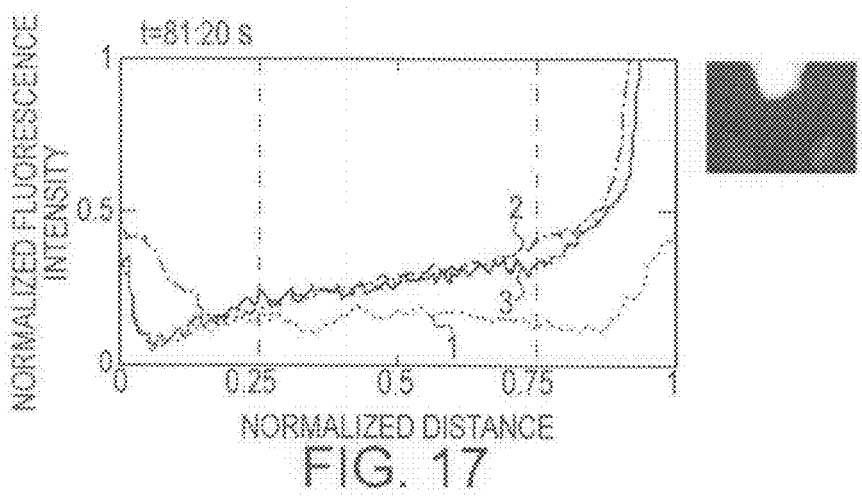
FIG. 17 is a graph of light intensity after yet another period of time as measured along the lines referenced in FIG. 14.
Figure 18:
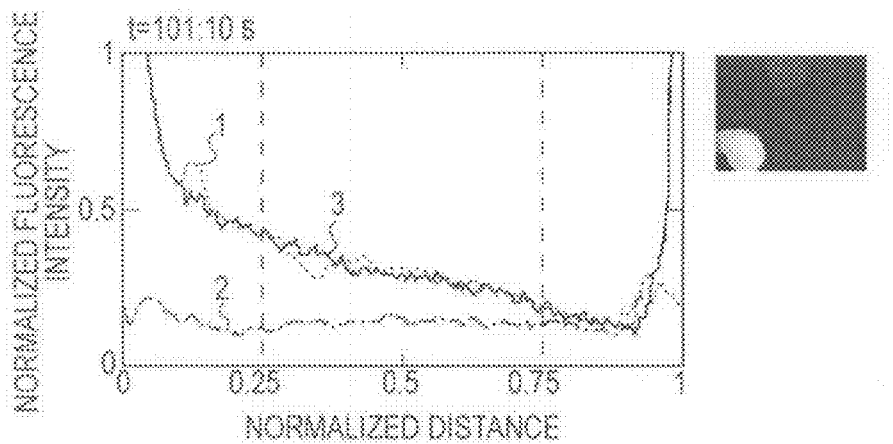
FIG. 18 is a graph of light intensity after yet another period of time as measured along the lines referenced in FIG. 14.
Figure 19:
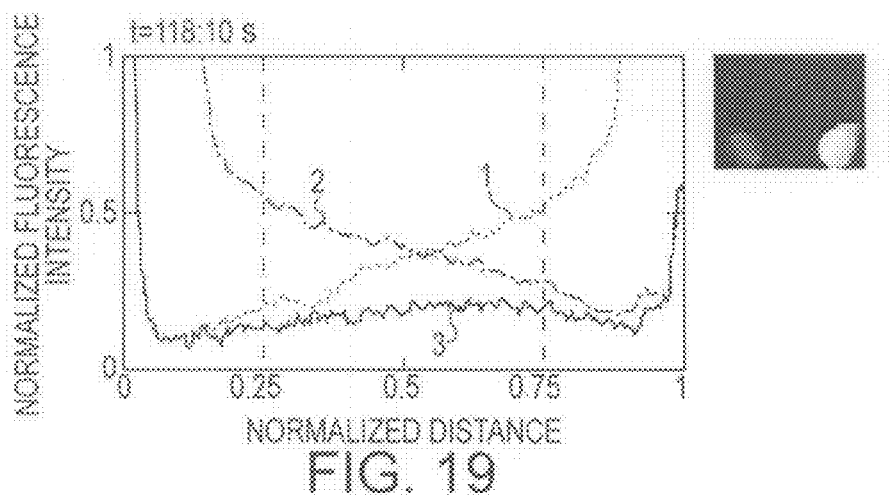
FIG. 19 is a graph of light intensity after yet another period of time as measured along the lines referenced in FIG. 14.
Figure 20:
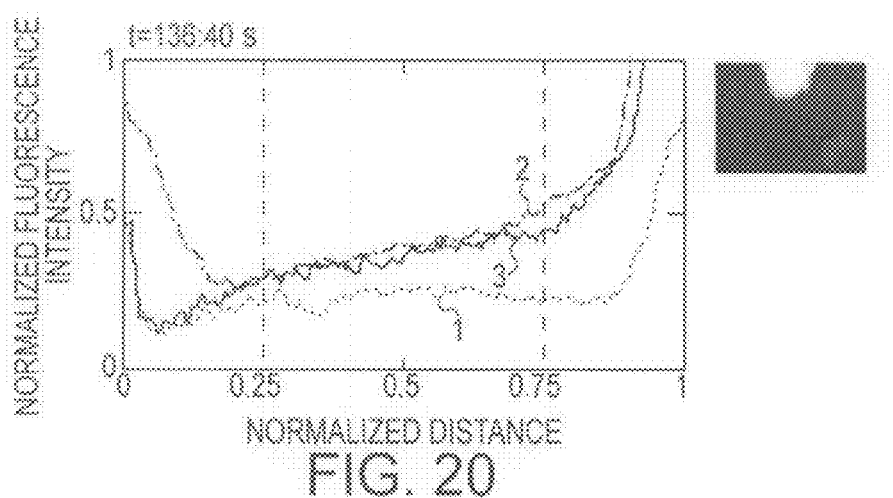
FIG. 20 is a graph of light intensity after yet another period of time as measured along the lines referenced in FIG. 14.

Referring to FIG. 14, in order to characterize the gradient position, a light scan along lines 1-2 (designated as line 1), 2-3 (designated as line 2) and 3-1 (designated as line 3) with a frequency of 1 frame every 10 seconds was performed. The graphs in FIGS. 15-20 show light intensity as raw data, measured across lines 1, 2 and 3 in FIG. 14, at different sequential steps of two full cycles. FIGS. 15-17 correspond to the first cycle and FIGS. 18-20 correspond the second cycle. FIGS. 15-18 show the evolution of the gradient as it performs a full rotation around its center. The entire sequence and investigation was performed in 136 minutes and 40 seconds.

FIGS. 15-20 demonstrate the robustness and repeatability of the gradient formation. In each set of figures, the conditions were the same but the figures correspond to a different cycle. The intensity of the light source exhibited sudden changes throughout the investigation that modified the values of all the lines scanned 1, 2 and 3 (the data shown in the graphs is raw, i.e. without corrections), however, the relative values remained constant. The overlay of lines 1 and 2 in FIGS. 15, 18 and lines 2 and 3 in FIGS. 19, 20 reveals the symmetry of the diffusive field across the chamber and is indicative of the absence of convection.

With the present configuration, decoupling the light signal produced in the chamber from the signal produced at the access ports is challenging, especially at the edges of the line scans, i.e. segments [0-0.25] and [0.75-1]. These effects are due to the difference of light intensity between access ports (500 μm deep) and chamber (3 μm deep), and reflection at the edges. A mask covering the ports could be used to reduce the problem, and thus, the present invention includes such.

The present invention provides methods for selectively modifying a concentration gradient of one or more agents in liquid. The methods involve flowing liquid and agent through at least one of the channels of a microfluidic device as described herein, whereby at least a portion of the agent is then diffusively transferred through the aperture(s) into the chamber thereby forming the concentration gradient. The concentration gradient can be modified in various fashions. For example, the gradient can be modified by changing the concentration of agent in the liquid flowing through at least one channel. The gradient can also be modified by changing the flow rate of liquid and agent in at least one of the channels. And, the gradient can be modified by selecting a different channel in which the liquid and agent flows.

Bacterial Chemotaxis in a Microfluidic Device

Chemotaxis, a kind of taxis, is a phenomenon in which bodily cells, bacteria, and other single-cell or multicellular organisms direct their movements according to certain chemicals in their environment. This is important for bacteria to find food (for example, glucose) by moving towards the highest concentration of food molecules, or to flee from poisons (for example, phenol).

Bacterial chemotaxis is typically more difficult to quantify than chemotaxis of adherent cells (e.g. fibroblasts) because bacteria need to be in suspension, which makes this type of assay particularly sensitive to uncontrolled convective flow. Bacterial chemotaxis is also difficult to quantify because bacteria usually move fast (such as about 30 μm/s), and in many cases faster than the time required for a controlled diffusive gradient to develop.

Generally, in chemotaxis studies, the present invention devices can greatly facilitate analyses of the effects of exposure of one or more agents upon cells, bacteria or other microorganisms. A "source well" or "source" as such is typically referred in the chemotaxis arts, can be formed by flowing one or more agents and liquid in a channel of the preferred devices herein. A "sink" can be formed by flowing liquid such as a buffer liquid in another channel, devoid of any agent(s). Bacteria or other microorganisms can be introduced into the chamber by administering the bacteria into liquid flowing in another channel, whereby they then can move into the chamber through an access port. It is also contemplated that the bacteria could be introduced directly into the chamber or region of interest.

Figure 21:
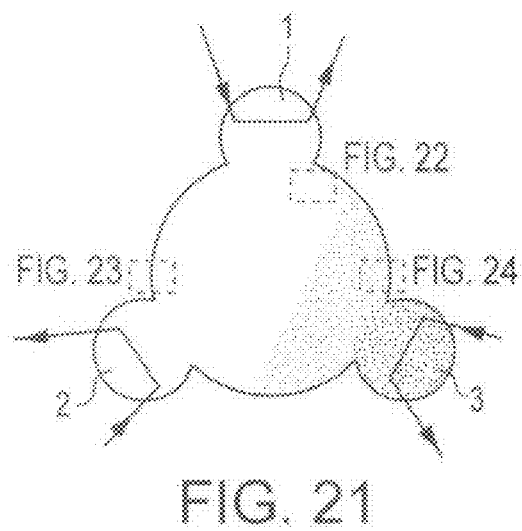
FIG. 21 is a schematic illustration of a chamber of the preferred embodiment device and locations at which various components were introduced in a chemotaxis investigation.
Figure 22:
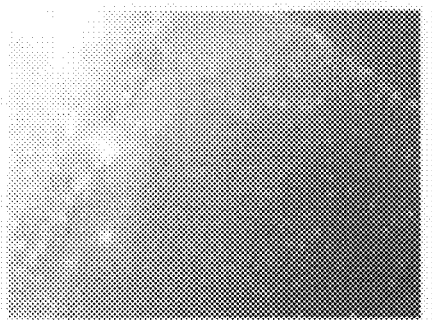
FIG. 22 is a photograph taken after a period of time at location a in the chamber of the device depicted in FIG. 21.
Figure 23:
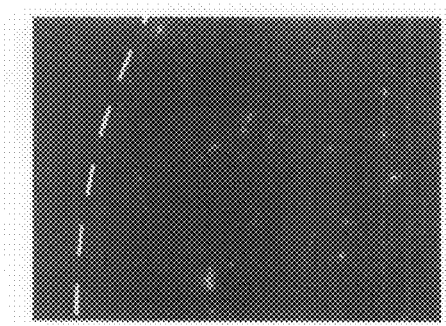
FIG. 23 is a photograph taken after a period of time at location b in the chamber of the device depicted in FIG. 21.
Figure 24:
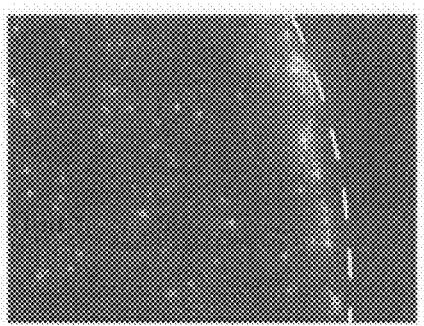
FIG. 24 is a photograph taken after a period of time at location c in the chamber of the device depicted in FIG. 21.
Figure 25:
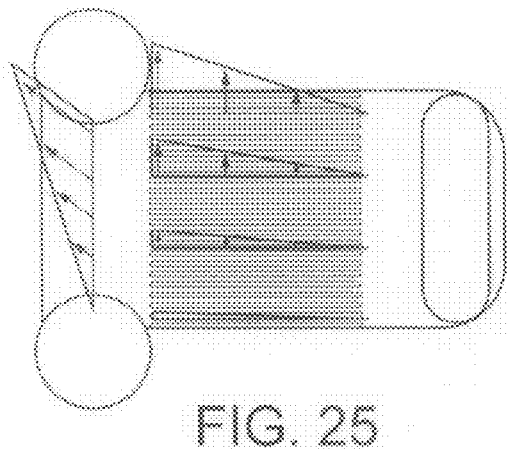
FIG. 25 is a schematic illustration of a multichannel microfluidic device used in another chemotaxis investigation.

Two dimensional chemotaxis inside a microfluidic device was demonstrated with *Psuedomona Aeruginosa*, a gram negative bacteria and opportunistic pathogen broadly used as a model system, as shown in FIG. 21. Chemotactic media, i.e. glucose, was introduced in the microfluidic device through access port 3 and regular media, i.e. buffer, through access ports 1 and 2, FIG. 22. After the gradient reached steady state, after typically 15 minutes, the flows were stopped, the syringe connected to access port 1 was switched with another syringe containing 1 ml of bacterial solution, and all the flow rates were set to 0.1 ml/h for two hours, after which bacterial activity was monitored. FIG. 22 shows bacterial activity adjacent to the access port 1. Bacteria were not introduced in the chamber; rather, they entered as a result of their random diffusion once the chemical gradient was established at access port 3. Higher colony activity was observed close to the access port where the chemotractant was delivered. FIG. 23 illustrates a relatively low population of bacteria at access port 2, where only a buffer liquid existed. FIG. 24 illustrates a relatively high population of the bacteria at access port 3, where the glucose was delivered.

This investigation demonstrates the capability of the preferred embodiment microfluidic devices to be used for bacterial chemotactic experiments without convection, where bacteria are introduced to the chamber after the gradient is fully developed. This demonstration enables the quantification of, for example, the effects of variable diffusive gradients and of two dimensional combinations of chemotractants and chemorepellants on bacterial chemotaxis. The present invention methods and various devices are believed to be particularly useful in association with forming, maintaining, and investigating biomolecular gradients and their effect upon cellular systems. An excellent description of various approaches, devices, and strategies in this field is provided in T. M. Keenan and A. Folch, "Biomolecular Gradients in Cell Culture Systems," *Lab Chip,* 2008, 8, 34-57.

Therefore, a new class of microfluidic devices is provided that allows for the generation of diffusive chemical gradients with exquisite spatiotemporal tunability, demonstrated for example, by a controlled rotation of a gradient inside a circular chamber. The microfluidic devices also allow for the maintenance of a chemical gradient at any arbitrary angle, and the device may find applications in the temporal induction of cellular polarization.

Figure 26:
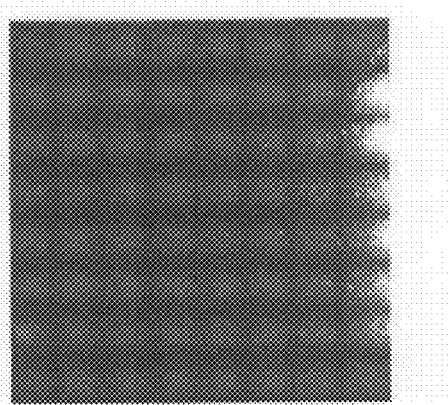
FIG. 26 is a photograph illustrating a gradient along the multichannels of the device depicted in FIG. 25 after a period of time.
Figure 27:
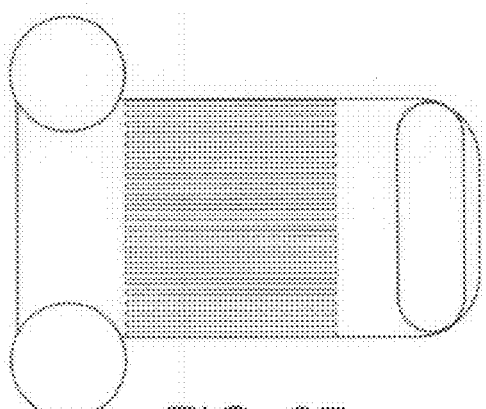
FIG. 27 is a schematic illustration of the multichannel microfluidic device and location of an evaluation location in the chemotaxis investigation.
Figure 28:
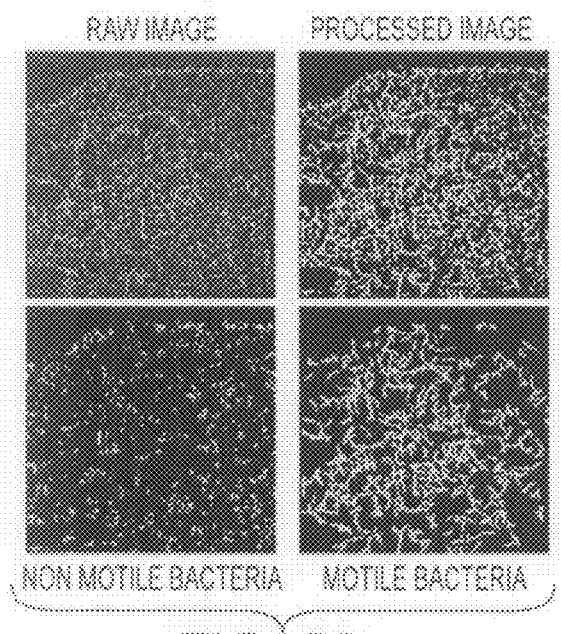
FIG. 28 includes several images of bacteria as observed at the evaluation location noted in FIG. 27.
Figure 29:
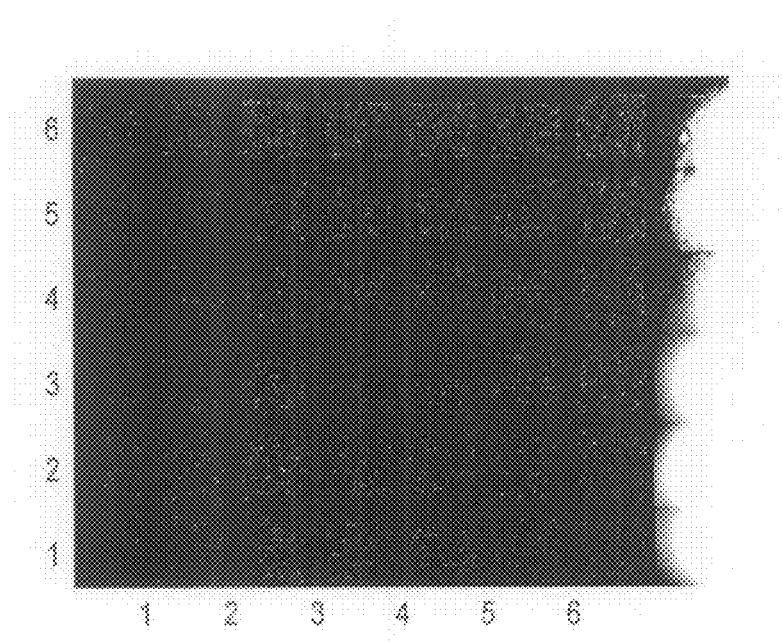
FIG. 29 is a photograph and associated graphs illustrating a gradient of non-motile bacteria from the chemotaxis investigation referenced in FIG. 25.
Figure 29:
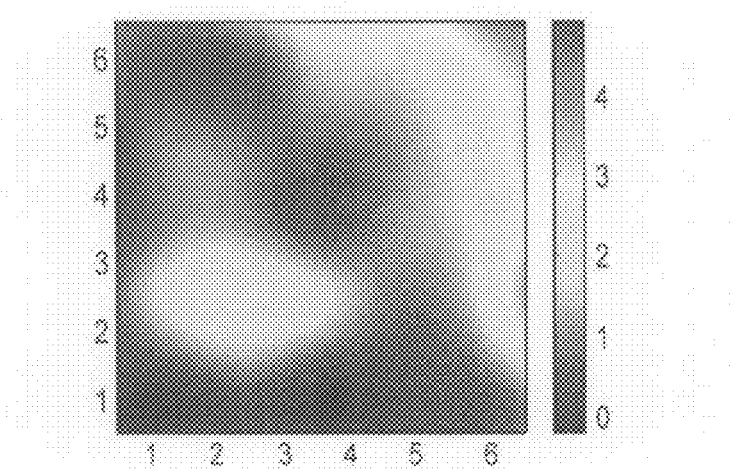
Figure 29:
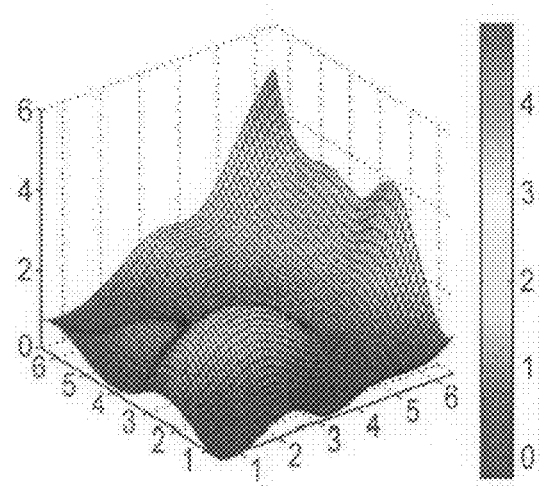
Figure 30:
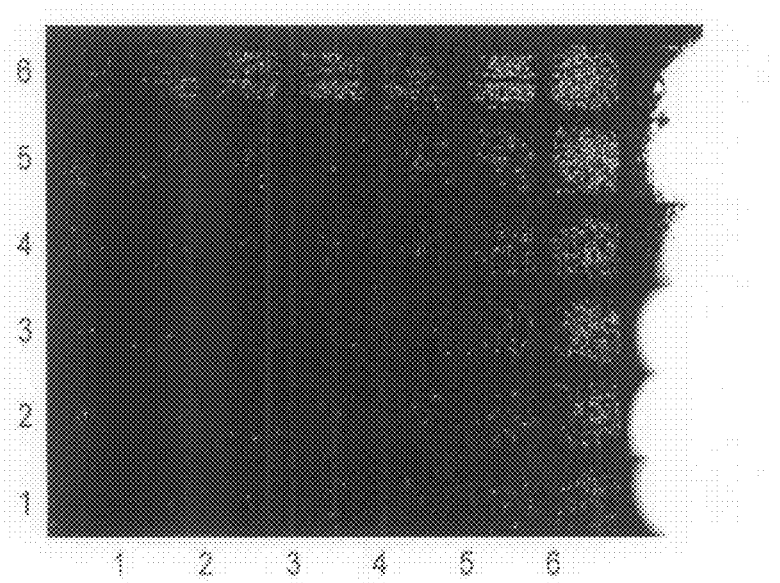
FIG. 30 is a photograph and associated graphs illustrating a gradient of motile bacteria from the chemotaxis investigation referenced in FIG. 25.
Figure 30:
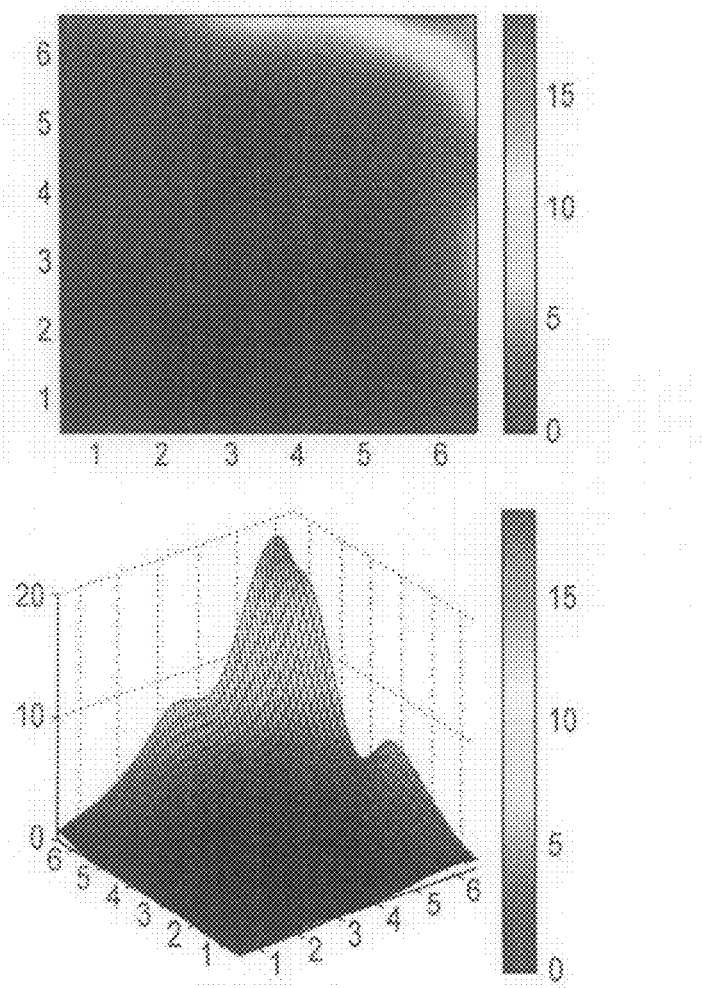

FIGS. 25-30 illustrate aspects of another chemotaxis investigation performed in accordance with the practices and devices of the present invention. In this investigation, the chamber was modified to include "horizontal spacers" that constrain geometrically the formation of the gradient. The result is a concentration gradient that forms vertically between upper and lower access ports, and a sequence of perpendicular concentration gradients of constant slope between the left and right sides of the chamber. Each horizontal concentration gradient has a different slope. This characteristic enables testing of bacterial chemotaxis when the bacteria are exposed to different gradients, in a high throughput manner. In contrast, currently known prior art chambers such as the Dunn chamber (i.e. a special single round cell chambered slide), only allow for testing one concentration gradient at a time. FIG. 26 shows a mosaic of stitched pictures showing bacterial activity in the chamber. FIG. 28 shows a small region of the chamber (top right side) next to the access port where the bacteria enter the chamber. Using Matlab® (a numerical computing environment and programming language available from the MathWorks Corp. of Natick, Mass.), the images were processed to quantify the number of motile and non-motile bacteria upon exposure to glucose (the same experiment as with the previously noted chamber). FIG. 29 shows the distribution of non-motile bacteria 24 hours after starting the experiment, and FIG. 30 illustrates the distribution of motile bacteria.

The preferred embodiment microfluidic devices are robust, the generation of the gradients is repeatable, and the devices can be readily disassembled, cleaned and reassembled again for another use. It is contemplated that this new microfluidic tool will have a broad impact in different fields, ranging from cell culture and toxicity to the development of complex and in-vivo like models of cell interactions within organisms.

Additional Applications

In addition to the various applications and uses described herein, it is contemplated that the present invention will find use in a broad range of fields and areas. For example, and as previously indicated, the present invention systems and devices can be used in chemotaxis studies such as in research directed to aspects of the immune system and behavior of bacteria or other microorganisms. A wide array of investigations can be conducted using diverse microorganisms, such as mammalian cells and/or eukaryotic cells.

The present invention can also be used in protein crystallization studies. In this regard for example, the effects of varying concentration(s) of agent(s) in a liquid undergoing (or about to undergo) crystallization can be readily assessed.

The present invention can also be used in a host of drug screening applications involving the effects of agent concentration or changing concentrations upon cells or other microorganisms. For example, combinations of different drugs can be screened as for their effect upon specific cancers.

Sensitivity of cells or other microorganisms can be assessed with regard to chemical pollutants, drugs, nanoparticles, and other agents.

It is also contemplated that an array of strategies could be undertaken directed to personalized medicine. For example, personalized chemotherapies can be investigated in which cells from a biopsy are introduced into a microfluidic device chamber and one or more drugs are administered into liquids flowing through the device channels. For the three channel device described herein, drug A could be added to a liquid flowing in a first channel, and drug B could be added to a liquid flowing in a second channel or a second and a third channel. Resulting concentration gradients of drugs A and B are established in the chamber. And, the location of the greatest number of deaths of cancerous cells in the chamber is determined, which can then be used to assess an optimal combination or proportions of drugs A and B.

Yet another significant application of the present invention is in the formation and maintenance of diffusion waves. This could allow temporal quantification or other time-based studies of cell responses to various signals. For example, cells or other microorganisms could be introduced into a device chamber and then nutrients diffusively transferred into the chamber through one or more access ports, and a drug or other molecular signal diffusively transferred into the chamber by another access port. The response of cells to changes in concentrations of the nutrients and/or drugs can then be readily undertaken.

An interesting application for motile microorganisms such as motile bacteria, involves inducing movement of the bacteria from one location to another in a microfluidic chamber by establishing particular concentration gradients of agents to which the bacteria exhibit a response. Related to this, is a strategy in which the gradient is changed or otherwise altered or moved in the chamber, thereby causing a response such as movement, by the bacteria.

Various crystallization investigations can also be undertaken using the present invention system and devices. For example, in a system comprising multiple reagents or agents, crystallization of the system may depend upon the proportions of agents. That is, crystallization may occur for certain combinations of agents in particular concentrations or ranges of concentrations. Identification of the locations in the chamber of crystal nucleation can then indicate the concentrations of agents at these locations. And, moreover, once a preferred combination of components and proportions has been identified, the present invention system and devices can be used to better identify the most preferred concentrations of components.

Additional investigations concerning nanotoxicity and controlled simulation of the interaction between different populations of cells can be undertaken using the present invention. For example, multiple microfluidic chambers may contain cells, and nutrients diffusively transferred into the chamber. One or more channels of the multiple chambers receive a flow of one or more agents that is recirculated between the multiple chambers. As the one or more agents such as nanoparticles are diffusively transferred into the chambers, the effects upon the cells can be assessed.

In addition, a broad range of applications are contemplated in the medical field. For example, the invention may be practiced by identifying a region or portion of a patient's body, and designating that region as a chamber. Multiple catheters or other conduits are appropriately posited in or proximate the region of interest. Small apertures are formed in each of the catheters and the catheters configured such that the apertures are located at a tip or distal end of a catheter. Liquids potentially carrying drugs or other agents are then flowed through the catheters in accordance with the present invention, and preferably such that flow rates in each of the catheters is matched. Diffusive transport of drugs then occurs from the catheters, through the respective apertures, and into the body region of interest. This practice would be highly localized to the region of interest, and would not introduce additional volumes of liquid.

Materials and Methods

The following materials and methods were used in several of the previously described preferred embodiment microfluidic devices.

A microfluidic chamber having dimensions of 1.5 mm in diameter and 10 µm deep, was wet etched using hydrofluoric acid on a 3 inch wide by 500 µm thick borosilicate glass wafer (Mark optics). Three access ports (1 mm in diameter and 500 µm deep) were drilled as through-holes on the glass wafer. A second glass wafer was bonded to the first glass wafer non-permanently as described herein. The PDMS gasket was fabricated using standard techniques using soft lithography. Channels in the gasket were typically 100 to 250 µm tall, and 500 to 1000 µm wide. Holes were formed at the end of the PDMS channels using 19 gauge stainless blunt needles.

Blunt 16-22 gauge needles were epoxied into the back of the PMMA plastic layer and connected to 1-way valves and plastic syringes via 0.625 mm ID microbore Tygon tubing (Cole-Parmer). Liquids were pumped using syringe pumps (Harvard Apparatus PHD 2000).

Channel design patterns for the PMMA plastic layer (McMaster-Carr) were drafted in Autocad 2007 (Autodesk), translated into G-codes by VisualMill 5.0 (MedSoft Corp.), and cut using a milling machine MicroMill 2000 (MicroProto Systems). PMMA vacuum channels were milled 0.5 mm deep and 0.4 mm wide. And, PMMA delivery channels were milled 1 mm deep and 1 mm wide.

6-carboxyfluorescein (FAM), was purchased from Invitrogen (Carlsbad, Calif.).

Image acquisition was performed using an inverted microscope Axiovert 200 (Zeiss) Color, a digital camera (CFW-1312c (Scion Corporation) and Labview (a platform and development environment for a visual programming language, available from National Institutes Co. of Austin, Tex.). Typically, in the dynamic investigations, images were acquired every 5 seconds or 10 seconds. Intensity of light was quantified from the pictures using Matlab® (Mathworks). The graphs show raw data.

Generally, *Pseudomonas aeruginosa*, a gram-negative bacteria and opportunistic pathogen was used, due to its wide use as a model system for bacterial biofilm studies. Bacterial cultures were prepared as described in R. C. Moulton and T. C. Montie, *J. Bacteriol*, 1979, 137, 274-280, by growing cells on minimal media with glucose, and then washing and suspending in phosphate buffered saline (PBS). Cells suspended in PBS were stained by contacting with a SYTO 9 green-fluorescent nucleic acid stain (using LIVE/DEAD BacLight, bacterial viability kit from Invitrogen of Carlsbad, (Calif.) at a final concentration of 2.08 µm for 30 minutes and then washed two times in chemotaxis media, as described in the previous article by Moulton et al.

Additional details regarding microfluidic devices, their configuration, their construction, pumps for moving liquids therein, and other aspects are provided in US Patent Application Publication Nos. 2008/0085219; 2007/0253868; and 2006/0002804. Additional aspects are described in U.S. Pat. No. 7,306,672. And still further details, aspects, and background information are provided in Saadi et al., "Generation of Stable Concentration Gradients in 2D and 3D Environments Using a Microfluidic Ladder Chamber," *Biomed Microdevices*, (2007), 9:627-635; Mosadegh et al., "Generation of Stable Complex Gradients Across Two-Dimensional Surfaces and Three-Dimensional Gels," *Langmuir*, (2007), 23, 10910-10912; Keenan et al., "Microfluidic 'Jets' for Generating Steady-State Gradients of Soluble Molecules on Open Surfaces," *Appl. Phys Lett.* 89, 114103 (2006); Abhyankar et al., "Characterization of a Membrane-Based Gradient Generator for Use in Cell-Signaling Studies," *Lab Chip*, (2006), 6, 389-393; Diao et al., "A Three-Channel Microfluidic Device for Generating Static Linear Gradients And its Application to the Quantitative Analysis of Bacterial Chemotaxis," *Lab Chip*, (2006), 6, 381-388; Jeon et al., "Neutrophil Chemotaxis in Linear and Complex Gradients of Interleukin-8 Formed in a Microfabricated Device," *Nat. Biotech*, Vol. 20, pp. 826-830 (August 2002); and Paliwal et al., "MAPK—Mediated Bimodal Gene Expression and Adaptive Gradient Sensing in Yeast," *Nature*, Vol. 446, 1 Mar. 2007, pp. 46-51.

Many other benefits will no doubt become apparent from future application and development of this technology.

All patents, published applications, and articles noted herein are hereby incorporated by reference in their entirety.

Each of the various features, aspects, and details of any of the embodiments described herein may be combined with any of the features, aspects and details of other embodiments described herein.

As described hereinabove, the present invention solves many problems associated with previous type devices and practices. However, it will be appreciated that various changes in the details, materials and arrangements of parts, which have been herein described and illustrated in order to explain the nature of the invention, may be made by those skilled in the art without departing from the principle and scope of the invention, as expressed in the appended claims.

What is claimed is:

1. A microfluidic system comprising:
   a chamber defining an interior region adapted for retaining a liquid;
   at least three channels adapted to contain and direct liquid when flowing therethrough, each channel defining an inlet and an outlet, each of the channels being in constant fluid communication with the chamber via a respective access port located between the inlet and outlet of the respective channel;
   at least one flow controller for matching flow rates of liquid flowing in the channels;
   wherein the microfluidic system is free from membranes disposed at or proximate the access ports that would otherwise affect fluid communication between a respective channel and the chamber.

2. The system of claim 1 further comprising:
   liquid in the chamber and liquid in at least two of the channels.

3. The system of claim 1 wherein the chamber is cylindrical in shape and the access ports are in the form of apertures accessible along a chamber wall, the apertures providing fluid communication between the chamber and a respective channel.

4. The system of claim 1 wherein the chamber is formed from a material selected from the group consisting of glass, ceramic, plastic, quartz, silicon, sapphire, metal, and combinations thereof.

5. The system of claim 1 wherein the chamber and each of the channels are sized such that the resistance to flow by a liquid through the chamber is at least 1000 times greater than resistance to flow by the liquid through a channel.

6. The system of claim 2 wherein the liquid in at least one of the channels includes at least one agent.

7. The system of claim 6 wherein the agent is soluble in the liquid.

8. The system of claim 6 wherein the system is configured such that after a period of time during which the liquid and agent are flowing past at least one access port, an amount of the agent diffuses through the respective access port into the chamber.

9. The system of claim 8 wherein at least one concentration gradient of the agent forms within the chamber.

10. A microfluidic system comprising:
    a chamber defining an interior region adapted for retaining a liquid;
    at least three channels adapted to contain and direct liquid when flowing therethrough, each of the channels being in constant fluid communication with the chamber via a respective access port, each channel defining an inlet and an outlet and all outlets being in fluid communication with one another at a junction, and each of the channels defining an outlet leg extending between a respective access port and the junction;
    wherein the system is free from membranes proximate the access ports that would otherwise affect fluid communication between a respective channel and the chamber.

11. The system of claim 10 wherein the outlet legs of each of the channels have equal resistance to flow.

12. The system of claim 10 further comprising:
    a liquid in the chamber and liquid in the channels.

13. The system of claim 10 wherein the chamber is cylindrical in shape and the access ports are in the form of apertures accessible along a chamber wall, the apertures providing fluid communication between the chamber and a respective channel.

14. The system of claim 10 wherein the chamber is formed from a material selected from the group consisting of glass, plastic, quartz, silicon, sapphire, metal, and combinations thereof.

15. The system of claim 10 wherein the chamber and each of the channels are sized such that resistance to flow by a liquid through the chamber is at least 1000 times greater than the resistance to flow by the liquid through a respective channel.

16. The system of claim 12 wherein the liquid includes at least one agent.

17. The system of claim 16 wherein the agent is soluble in the liquid.

18. The system of claim 16 wherein the system is configured such that after a period of time during which the liquid and agent are flowing past at least one access port, an amount of the agent diffuses through the respective access port into the chamber.

19. The system of claim 18 wherein at least one concentration gradient of the agent forms within the chamber.

* * * * *